(12) United States Patent
Jeyakumaran

(10) Patent No.: US 12,280,203 B2
(45) Date of Patent: Apr. 22, 2025

(54) APPARATUSES AND METHODS FOR NEGATIVE PRESSURE WOUND THERAPY

(71) Applicant: T.J.Smith and Nephew, Limited, Hull (GB)

(72) Inventor: Vithushan Jeyakumaran, London (GB)

(73) Assignee: T.J.Smith and Nephew, Limited, Hull (GB)

( * ) Notice: Subject to any disclaimer, the term of this patent is extended or adjusted under 35 U.S.C. 154(b) by 386 days.

(21) Appl. No.: 17/762,698

(22) PCT Filed: Oct. 1, 2020

(86) PCT No.: PCT/EP2020/077478
§ 371 (c)(1),
(2) Date: Mar. 22, 2022

(87) PCT Pub. No.: WO2021/064085
PCT Pub. Date: Apr. 8, 2021

(65) Prior Publication Data
US 2022/0395630 A1    Dec. 15, 2022

(30) Foreign Application Priority Data

Oct. 3, 2019 (GB) .................................... 1914283

(51) Int. Cl.
*A61M 1/00* (2006.01)
(52) U.S. Cl.
CPC .............. *A61M 1/98* (2021.05); *A61M 1/912* (2021.05)

(58) Field of Classification Search
CPC .......... A61M 1/98; A61M 1/912; A61M 1/00; A61F 13/05; B01D 2319/00
See application file for complete search history.

(56) References Cited

U.S. PATENT DOCUMENTS

| 730,062 A | 6/1903 | Widmer |
| 2,468,445 A | 4/1949 | Kenneth et al. |
| D239,019 S | 3/1976 | Flinn |
| (Continued) | | |

FOREIGN PATENT DOCUMENTS

| CN | 2623320 Y | 7/2004 |
| DE | 4312852 A1 | 10/1993 |
| (Continued) | | |

OTHER PUBLICATIONS

Fong K.D., et al., "SNaP Wound Care System: Ultraportable Mechanically Powered Negative Pressure Wound Therapy," Advances in Wound Care, vol. 1(1), Feb. 2012, 4 pages.

(Continued)

*Primary Examiner* — Kai H Weng
*Assistant Examiner* — Alessandro R Del Priore
(74) *Attorney, Agent, or Firm* — Knobbe, Martens, Olson & Bear, LLP

(57) ABSTRACT

Disclosed herein are several embodiments of a negative pressure appliance and methods of using the same in the treatment of wounds. Some embodiments are directed to improved filter assemblies for use with in a canister for collecting wound exudate from a wound site, the canister comprising a filter and a shield configured to protect the filter from components within the interior of the canister.

19 Claims, 15 Drawing Sheets

(56) References Cited

U.S. PATENT DOCUMENTS

| | | |
|---|---|---|
| 3,980,166 A | 9/1976 | de Feudis |
| 4,063,556 A | 12/1977 | Thomas et al. |
| 4,136,696 A | 1/1979 | Nehring |
| 4,203,445 A | 5/1980 | Jessup et al. |
| 4,228,798 A | 10/1980 | Deaton |
| 4,266,545 A | 5/1981 | Moss |
| 4,293,609 A | 10/1981 | Erickson |
| 4,321,020 A | 3/1982 | Mittal |
| 4,328,828 A * | 5/1982 | Cianci .................. F16K 11/022 251/339 |
| 4,331,147 A | 5/1982 | Armstrong |
| 4,498,850 A | 2/1985 | Perlov et al. |
| 4,569,674 A | 2/1986 | Phillips et al. |
| 4,578,060 A | 3/1986 | Huck et al. |
| 4,585,397 A | 4/1986 | Crawford et al. |
| 4,604,313 A | 8/1986 | Mcfarland et al. |
| 4,731,076 A | 3/1988 | Noon et al. |
| 4,758,238 A | 7/1988 | Sundblom et al. |
| 4,767,417 A | 8/1988 | Boehringer et al. |
| 4,826,494 A | 5/1989 | Richmond et al. |
| 4,832,299 A | 5/1989 | Gorton et al. |
| 4,840,770 A | 6/1989 | Walz et al. |
| 4,865,816 A | 9/1989 | Walz et al. |
| 4,870,975 A | 10/1989 | Cronk et al. |
| 4,979,944 A | 12/1990 | Luzsicza |
| 4,988,344 A | 1/1991 | Reising et al. |
| 4,988,345 A | 1/1991 | Reising |
| 5,071,104 A | 12/1991 | Witt et al. |
| 5,135,485 A | 8/1992 | Cohen et al. |
| 5,141,504 A | 8/1992 | Herweck et al. |
| 5,156,602 A | 10/1992 | Steffler |
| 5,219,428 A | 6/1993 | Stern |
| 5,246,353 A | 9/1993 | Sohn |
| D352,463 S | 11/1994 | Kubo |
| 5,360,445 A | 11/1994 | Goldowsky |
| 5,386,735 A | 2/1995 | Langdon |
| 5,397,299 A | 3/1995 | Karwoski et al. |
| D357,735 S | 4/1995 | McPhee |
| 5,411,474 A | 5/1995 | Ott et al. |
| 5,458,586 A | 10/1995 | Adiletta |
| 5,466,229 A | 11/1995 | Elson et al. |
| 5,484,428 A | 1/1996 | Drainville et al. |
| 5,514,088 A | 5/1996 | Zakko |
| 5,582,601 A | 12/1996 | Wortrich et al. |
| 5,584,824 A | 12/1996 | Gillette et al. |
| 5,591,297 A | 1/1997 | Ahr |
| 5,630,855 A | 5/1997 | Lundback |
| 5,656,027 A | 8/1997 | Ellingboe |
| 5,669,892 A | 9/1997 | Keogh et al. |
| 5,685,214 A | 11/1997 | Neff et al. |
| 5,693,013 A | 12/1997 | Geuder |
| 5,707,173 A | 1/1998 | Cottone et al. |
| 5,712,795 A | 1/1998 | Layman et al. |
| 5,785,700 A | 7/1998 | Olson |
| 5,787,928 A | 8/1998 | Allen et al. |
| 5,807,359 A | 9/1998 | Bemis et al. |
| D400,249 S | 10/1998 | Holubar |
| 5,876,387 A | 3/1999 | Killian et al. |
| 5,882,743 A | 3/1999 | McConnell |
| D408,625 S | 4/1999 | Barker |
| 5,960,837 A | 10/1999 | Cude |
| 6,010,527 A | 1/2000 | Augustine et al. |
| 6,027,490 A | 2/2000 | Radford et al. |
| 6,075,177 A | 6/2000 | Bahia et al. |
| 6,099,493 A | 8/2000 | Swisher |
| 6,102,205 A | 8/2000 | Greff et al. |
| 6,168,758 B1 | 1/2001 | Forsberg et al. |
| 6,203,291 B1 | 3/2001 | Stemme et al. |
| 6,232,680 B1 | 5/2001 | Bae et al. |
| D449,891 S | 10/2001 | Moro |
| 6,352,233 B1 | 3/2002 | Barberich |
| D456,514 S | 4/2002 | Brown et al. |
| 6,395,955 B1 | 5/2002 | Roe et al. |
| 6,396,407 B1 | 5/2002 | Kobayashi |
| 6,468,199 B1 | 10/2002 | Satou et al. |
| 6,501,002 B1 | 12/2002 | Roe et al. |
| 6,547,255 B1 | 4/2003 | Donaway et al. |
| D475,132 S | 5/2003 | Randolph |
| 6,575,333 B1 | 6/2003 | Raboin |
| D477,869 S | 7/2003 | Vijfvinkel |
| D478,659 S | 8/2003 | Hall et al. |
| 6,620,379 B1 | 9/2003 | Piuk et al. |
| D481,459 S | 10/2003 | Nahm |
| 6,723,430 B2 | 4/2004 | Kurata et al. |
| 6,755,807 B2 | 6/2004 | Risk, Jr. et al. |
| 6,764,462 B2 | 7/2004 | Risk, Jr. et al. |
| 6,800,074 B2 | 10/2004 | Henley et al. |
| 6,820,483 B1 | 11/2004 | Beckerman |
| 6,856,821 B2 | 2/2005 | Johnson |
| 6,885,116 B2 | 4/2005 | Knirck et al. |
| D504,953 S | 5/2005 | Ryan |
| D516,217 S | 2/2006 | Brown et al. |
| 7,004,915 B2 | 2/2006 | Boynton et al. |
| D522,657 S | 6/2006 | Murphy et al. |
| 7,066,949 B2 | 6/2006 | Gammons et al. |
| 7,070,584 B2 | 7/2006 | Johnson et al. |
| 7,128,735 B2 | 10/2006 | Weston |
| 7,153,294 B1 | 12/2006 | Farrow |
| D537,944 S | 3/2007 | Eda et al. |
| 7,198,046 B1 | 4/2007 | Argenta et al. |
| 7,214,202 B1 | 5/2007 | Vogel et al. |
| D544,092 S | 6/2007 | Lewis |
| 7,240,676 B2 | 7/2007 | Rutter |
| D548,347 S | 8/2007 | Ichino et al. |
| D551,578 S | 9/2007 | Kuriger et al. |
| D565,177 S | 3/2008 | Locke et al. |
| 7,367,342 B2 | 5/2008 | Butler |
| D580,285 S | 11/2008 | Hendrickson et al. |
| D581,042 S | 11/2008 | Randolph et al. |
| D581,522 S | 11/2008 | Randolph et al. |
| D585,137 S | 1/2009 | Onoda et al. |
| 7,503,910 B2 | 3/2009 | Adahan |
| D590,934 S | 4/2009 | Randolph et al. |
| 7,524,315 B2 | 4/2009 | Blott et al. |
| D593,676 S | 6/2009 | Locke et al. |
| D594,114 S | 6/2009 | Locke et al. |
| 7,553,306 B1 | 6/2009 | Hunt et al. |
| 7,569,742 B2 | 8/2009 | Haggstrom et al. |
| 7,604,610 B2 | 10/2009 | Shener et al. |
| 7,608,066 B2 | 10/2009 | Vogel |
| 7,615,036 B2 | 11/2009 | Joshi et al. |
| 7,625,362 B2 | 12/2009 | Boehringer et al. |
| 7,670,323 B2 | 3/2010 | Hunt et al. |
| D617,094 S | 6/2010 | Pidgeon et al. |
| D617,461 S | 6/2010 | Kaushal et al. |
| 7,731,702 B2 | 6/2010 | Bybordi et al. |
| 7,758,554 B2 | 7/2010 | Lina et al. |
| 7,794,450 B2 | 9/2010 | Blott et al. |
| D625,801 S | 10/2010 | Pidgeon et al. |
| 7,837,673 B2 | 11/2010 | Vogel |
| 7,846,141 B2 | 12/2010 | Weston |
| 7,857,806 B2 | 12/2010 | Karpowicz et al. |
| D630,313 S | 1/2011 | Pidgeon et al. |
| D630,725 S | 1/2011 | Pidgeon et al. |
| 7,862,339 B2 | 1/2011 | Mulligan |
| D635,588 S | 4/2011 | Sprules |
| 7,927,318 B2 | 4/2011 | Risk, Jr. et al. |
| 7,927,319 B2 | 4/2011 | Lawhorn |
| 7,976,598 B2 * | 7/2011 | Matula ............... B01D 46/0086 55/342 |
| D644,250 S | 8/2011 | Barber et al. |
| 7,998,125 B2 | 8/2011 | Weston |
| 8,021,348 B2 | 9/2011 | Risk, Jr. et al. |
| 8,048,046 B2 | 11/2011 | Hudspeth et al. |
| 8,061,360 B2 | 11/2011 | Locke et al. |
| 8,062,272 B2 | 11/2011 | Weston |
| 8,066,243 B2 | 11/2011 | Svedman et al. |
| D650,894 S | 12/2011 | Gonzalez |
| 8,070,735 B2 | 12/2011 | Koch et al. |
| D654,164 S | 2/2012 | Cole et al. |
| 8,162,909 B2 | 4/2012 | Blott et al. |
| D660,409 S | 5/2012 | Taggerty et al. |
| 8,167,869 B2 | 5/2012 | Wudyka |
| 8,172,817 B2 | 5/2012 | Michaels et al. |

(56) References Cited

U.S. PATENT DOCUMENTS

| | | |
|---|---|---|
| 8,202,262 B2 | 6/2012 | Lina et al. |
| 8,215,929 B2 | 7/2012 | Shen et al. |
| 8,216,197 B2 | 7/2012 | Simmons et al. |
| 8,226,620 B2 | 7/2012 | Giezendanner et al. |
| 8,240,470 B2 | 8/2012 | Pidgeon et al. |
| 8,257,327 B2 | 9/2012 | Blott et al. |
| 8,267,909 B2 | 9/2012 | Clementi et al. |
| 8,267,918 B2 | 9/2012 | Johnson et al. |
| 8,294,586 B2 | 10/2012 | Pidgeon et al. |
| 8,303,555 B2 | 11/2012 | Miau et al. |
| 8,317,774 B2 | 11/2012 | Adahan |
| 8,323,264 B2 | 12/2012 | Weston et al. |
| 8,333,744 B2 | 12/2012 | Hartwell et al. |
| 8,348,910 B2 | 1/2013 | Blott et al. |
| D675,728 S | 2/2013 | Tout et al. |
| 8,366,692 B2 | 2/2013 | Weston et al. |
| 8,372,049 B2 | 2/2013 | Jaeb et al. |
| 8,377,018 B2 | 2/2013 | Bendele et al. |
| 8,403,902 B2 | 3/2013 | Locke et al. |
| 8,409,160 B2 | 4/2013 | Locke et al. |
| 8,409,170 B2 | 4/2013 | Locke et al. |
| D681,806 S | 5/2013 | Kataoka et al. |
| 8,439,882 B2 | 5/2013 | Kelch |
| 8,444,392 B2 | 5/2013 | Turner et al. |
| 8,449,508 B2 | 5/2013 | Coulthard et al. |
| 8,480,641 B2 | 7/2013 | Jacobs |
| 8,494,349 B2 | 7/2013 | Gordon |
| 8,540,688 B2 | 9/2013 | Eckstein et al. |
| 8,617,129 B2 | 12/2013 | Hartwell |
| 8,641,693 B2 | 2/2014 | Locke et al. |
| 8,652,111 B2 | 2/2014 | Pratt et al. |
| 8,657,806 B2 | 2/2014 | Eckstein et al. |
| 8,668,677 B2 | 3/2014 | Eckstein et al. |
| 8,747,376 B2 | 6/2014 | Locke et al. |
| 8,771,259 B2 | 7/2014 | Karpowicz et al. |
| 8,814,840 B2 | 8/2014 | Evans et al. |
| 8,814,841 B2 | 8/2014 | Hartwell |
| 8,814,842 B2 | 8/2014 | Coulthard et al. |
| 8,843,327 B2 | 9/2014 | Vernon-Harcourt et al. |
| 8,858,517 B2 | 10/2014 | Pan et al. |
| 8,905,985 B2 | 12/2014 | Allen et al. |
| 8,974,429 B2 | 3/2015 | Gordon et al. |
| 9,019,681 B2 | 4/2015 | Locke et al. |
| 9,084,845 B2 | 7/2015 | Adie et al. |
| 9,138,531 B2 | 9/2015 | Yodfat et al. |
| 9,155,821 B2 | 10/2015 | Wudyka |
| 9,199,010 B2 | 12/2015 | Yao et al. |
| 9,211,486 B2 | 12/2015 | Locke et al. |
| D750,222 S | 2/2016 | Chang |
| D750,235 S | 2/2016 | Maurice |
| 9,320,838 B2 | 4/2016 | Hartwell et al. |
| D757,260 S | 5/2016 | Lombardi, III et al. |
| 9,327,063 B2 | 5/2016 | Locke et al. |
| 9,333,281 B2 | 5/2016 | Giezendanner et al. |
| 9,393,354 B2 | 7/2016 | Freedman et al. |
| 9,408,954 B2 | 8/2016 | Gordon et al. |
| 9,415,199 B2 | 8/2016 | Tsai |
| 9,427,505 B2 | 8/2016 | Askem et al. |
| 9,445,948 B2 | 9/2016 | Smola |
| D773,658 S | 12/2016 | Bow |
| 9,561,312 B2 | 2/2017 | Heaton et al. |
| 9,586,036 B2 | 3/2017 | Masuda et al. |
| D788,293 S | 5/2017 | Eckstein et al. |
| 9,636,440 B2 | 5/2017 | Weston et al. |
| D791,939 S | 7/2017 | Turturro et al. |
| D792,586 S | 7/2017 | Becker |
| D797,275 S | 9/2017 | Evans et al. |
| 9,801,984 B2 | 10/2017 | Braga et al. |
| D802,744 S | 11/2017 | Bjelovuk et al. |
| 9,901,664 B2 | 2/2018 | Askem |
| D813,374 S | 3/2018 | Bjelovuk et al. |
| D814,016 S | 3/2018 | Bjelovuk et al. |
| 9,923,401 B2 | 3/2018 | Jung |
| D815,726 S | 4/2018 | Bjelovuk et al. |
| D815,727 S | 4/2018 | Bjelovuk et al. |
| 9,956,325 B2 | 5/2018 | Malhi |
| D820,980 S | 6/2018 | Maurice |
| 10,004,835 B2 | 6/2018 | Wiesner |
| 10,124,093 B1 | 11/2018 | Francis et al. |
| 10,143,785 B2 | 12/2018 | Adams et al. |
| 10,155,070 B2 | 12/2018 | Childress et al. |
| 10,207,031 B2 | 2/2019 | Toth |
| D842,460 S | 3/2019 | Gierse et al. |
| D851,759 S | 6/2019 | Jones et al. |
| D852,356 S | 6/2019 | Steele et al. |
| 10,328,188 B2 | 6/2019 | Deutsch et al. |
| D888,225 S | 6/2020 | Askem |
| 10,898,621 B2 | 1/2021 | Chen et al. |
| 11,376,357 B2 | 7/2022 | Aarestad et al. |
| 12,064,546 B2 | 8/2024 | Askem et al. |
| 2002/0013545 A1 | 1/2002 | Soltanpour et al. |
| 2002/0026160 A1 | 2/2002 | Takahashi et al. |
| 2002/0030002 A1 | 3/2002 | Verkaart et al. |
| 2002/0098097 A1 | 7/2002 | Singh |
| 2002/0145012 A1 | 10/2002 | Ho |
| 2003/0101826 A1 | 6/2003 | Neubert |
| 2003/0163101 A1 | 8/2003 | Say |
| 2003/0164600 A1 | 9/2003 | Dunn et al. |
| 2003/0181850 A1 | 9/2003 | Diamond et al. |
| 2003/0212357 A1 | 11/2003 | Pace |
| 2003/0235635 A1 | 12/2003 | Fong et al. |
| 2004/0006321 A1 | 1/2004 | Cheng et al. |
| 2004/0064132 A1 | 4/2004 | Boehringer et al. |
| 2004/0068224 A1 | 4/2004 | Couvillon, Jr. et al. |
| 2004/0087918 A1 | 5/2004 | Johnson, III et al. |
| 2004/0102743 A1 | 5/2004 | Walker |
| 2004/0153029 A1 | 8/2004 | Blischak et al. |
| 2004/0167482 A1 | 8/2004 | Watson |
| 2004/0180093 A1 | 9/2004 | Burton et al. |
| 2004/0233631 A1 | 11/2004 | Lord |
| 2005/0124966 A1 | 6/2005 | Karpowicz et al. |
| 2005/0144711 A1 | 7/2005 | Valadez et al. |
| 2005/0166683 A1 | 8/2005 | Krivitski et al. |
| 2005/0187528 A1 | 8/2005 | Berg |
| 2005/0209560 A1 | 9/2005 | Boukhny et al. |
| 2005/0234485 A1 | 10/2005 | Seegert et al. |
| 2005/0248045 A1 | 11/2005 | Anthony |
| 2006/0029675 A1 | 2/2006 | Ginther |
| 2006/0059980 A1 | 3/2006 | Matsubara et al. |
| 2006/0129137 A1 | 6/2006 | Lockwood et al. |
| 2006/0144440 A1 | 7/2006 | Merkle |
| 2006/0280650 A1 | 12/2006 | Wong et al. |
| 2006/0281398 A1 | 12/2006 | Yokomizo et al. |
| 2007/0021697 A1 | 1/2007 | Ginther et al. |
| 2007/0032741 A1 | 2/2007 | Hibner et al. |
| 2007/0055209 A1 | 3/2007 | Patel et al. |
| 2007/0078444 A1 | 4/2007 | Larsson |
| 2007/0118096 A1 | 5/2007 | Smith et al. |
| 2007/0135779 A1 | 6/2007 | Lalomia et al. |
| 2007/0180904 A1 | 8/2007 | Gao |
| 2007/0219513 A1* | 9/2007 | Lina ............ A61F 13/0203 604/304 |
| 2007/0219535 A1 | 9/2007 | Phung et al. |
| 2007/0233022 A1 | 10/2007 | Henley et al. |
| 2007/0260226 A1 | 11/2007 | Jaeb et al. |
| 2008/0005000 A1 | 1/2008 | Radl et al. |
| 2008/0011667 A1 | 1/2008 | Ruschke |
| 2008/0015526 A1 | 1/2008 | Reiner et al. |
| 2008/0033400 A1 | 2/2008 | Holper et al. |
| 2008/0051708 A1 | 2/2008 | Kumar et al. |
| 2008/0082040 A1 | 4/2008 | Kubler et al. |
| 2008/0082077 A1 | 4/2008 | Williams |
| 2008/0125697 A1 | 5/2008 | Gao |
| 2008/0125698 A1 | 5/2008 | Gerg et al. |
| 2008/0183233 A1 | 7/2008 | Koch et al. |
| 2008/0243096 A1 | 10/2008 | Svedman |
| 2008/0281281 A1 | 11/2008 | Meyer et al. |
| 2009/0005746 A1 | 1/2009 | Nielsen et al. |
| 2009/0043268 A1 | 2/2009 | Eddy et al. |
| 2009/0099519 A1 | 4/2009 | Kaplan |
| 2009/0101219 A1 | 4/2009 | Martini et al. |
| 2009/0204049 A1 | 8/2009 | Lee |
| 2009/0216205 A1 | 8/2009 | Ryan et al. |
| 2009/0240218 A1 | 9/2009 | Braga et al. |

(56) References Cited

U.S. PATENT DOCUMENTS

| | | |
|---|---|---|
| 2009/0254066 A1 | 10/2009 | Heaton et al. |
| 2009/0299251 A1 | 12/2009 | Buan |
| 2009/0299306 A1 | 12/2009 | Buan |
| 2009/0312725 A1 | 12/2009 | Braga |
| 2010/0022990 A1 | 1/2010 | Karpowicz et al. |
| 2010/0030132 A1 | 2/2010 | Niezgoda et al. |
| 2010/0036333 A1 | 2/2010 | Schenk, III et al. |
| 2010/0121257 A1 | 5/2010 | King |
| 2010/0126268 A1 | 5/2010 | Baily et al. |
| 2010/0155465 A1 | 6/2010 | Mollstam et al. |
| 2010/0191178 A1 | 7/2010 | Ross et al. |
| 2010/0211030 A1 | 8/2010 | Turner et al. |
| 2010/0244780 A1 | 9/2010 | Turner et al. |
| 2010/0280435 A1 | 11/2010 | Raney et al. |
| 2010/0280536 A1 | 11/2010 | Hartwell |
| 2010/0305523 A1 | 12/2010 | Vess |
| 2010/0318043 A1 | 12/2010 | Malhi et al. |
| 2010/0318071 A1 | 12/2010 | Wudyka |
| 2011/0006876 A1 | 1/2011 | Moberg et al. |
| 2011/0015587 A1 | 1/2011 | Tumey et al. |
| 2011/0038741 A1 | 2/2011 | Lissner et al. |
| 2011/0054810 A1 | 3/2011 | Turner et al. |
| 2011/0060300 A1 | 3/2011 | Weig et al. |
| 2011/0063117 A1 | 3/2011 | Turner et al. |
| 2011/0066110 A1 | 3/2011 | Fathallah et al. |
| 2011/0071415 A1 | 3/2011 | Karwoski et al. |
| 2011/0076170 A1 | 3/2011 | Fujisaki et al. |
| 2011/0092927 A1 | 4/2011 | Wilkes et al. |
| 2011/0106027 A1 | 5/2011 | Vess et al. |
| 2011/0130712 A1 | 6/2011 | Topaz |
| 2011/0196291 A1 | 8/2011 | Vischer et al. |
| 2011/0251569 A1 | 10/2011 | Turner et al. |
| 2011/0257572 A1 | 10/2011 | Locke et al. |
| 2011/0313375 A1 | 12/2011 | Michaels |
| 2012/0000478 A1 | 1/2012 | Wagenhals |
| 2012/0001762 A1 | 1/2012 | Turner et al. |
| 2012/0035560 A1 | 2/2012 | Eddy et al. |
| 2012/0046624 A1 | 2/2012 | Locke et al. |
| 2012/0046625 A1 | 2/2012 | Johannison |
| 2012/0078181 A1 | 3/2012 | Smith et al. |
| 2012/0109083 A1 | 5/2012 | Coulthard et al. |
| 2012/0123323 A1 | 5/2012 | Kagan et al. |
| 2012/0123358 A1 | 5/2012 | Hall et al. |
| 2012/0181405 A1 | 7/2012 | Zlatic et al. |
| 2012/0184930 A1 | 7/2012 | Johannison |
| 2012/0220960 A1 | 8/2012 | Ruland |
| 2012/0226247 A1 | 9/2012 | Danei et al. |
| 2012/0259283 A1 | 10/2012 | Haase |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2013/0012772 A1 | 1/2013 | Gunday et al. |
| 2013/0025692 A1 | 1/2013 | Heide et al. |
| 2013/0053795 A1 | 2/2013 | Coulthard et al. |
| 2013/0131616 A1 | 5/2013 | Locke |
| 2013/0144227 A1 | 6/2013 | Locke et al. |
| 2013/0144235 A1 | 6/2013 | Augustine et al. |
| 2013/0165877 A1 | 6/2013 | Leeson et al. |
| 2013/0237937 A1 | 9/2013 | Ramella et al. |
| 2013/0267918 A1 | 10/2013 | Pan et al. |
| 2013/0270166 A1* | 10/2013 | Locke ............... B01D 19/0036 210/406 |
| 2013/0274718 A1 | 10/2013 | Yao et al. |
| 2014/0023533 A1 | 1/2014 | Ishii et al. |
| 2014/0100516 A1 | 4/2014 | Hunt et al. |
| 2014/0114236 A1 | 4/2014 | Gordon |
| 2014/0114237 A1 | 4/2014 | Gordon |
| 2014/0163490 A1 | 6/2014 | Locke et al. |
| 2014/0194835 A1 | 7/2014 | Ehlert |
| 2014/0276488 A1 | 9/2014 | Locke et al. |
| 2014/0276494 A1 | 9/2014 | Cisko et al. |
| 2014/0303551 A1 | 10/2014 | Germain et al. |
| 2014/0323906 A1 | 10/2014 | Peatfield et al. |
| 2015/0073363 A1 | 3/2015 | Kelch et al. |
| 2015/0094673 A1 | 4/2015 | Pratt et al. |
| 2015/0094674 A1 | 4/2015 | Pratt et al. |
| 2015/0100045 A1 | 4/2015 | Allen et al. |
| 2015/0174320 A1 | 6/2015 | Grant et al. |
| 2015/0231021 A1 | 8/2015 | Smith et al. |
| 2015/0246164 A1 | 9/2015 | Heaton et al. |
| 2015/0320916 A1 | 11/2015 | Croteau et al. |
| 2016/0015872 A1 | 1/2016 | Luckemeyer et al. |
| 2016/0015957 A1 | 1/2016 | Tieck et al. |
| 2016/0101278 A1 | 4/2016 | Norris et al. |
| 2016/0184498 A1 | 6/2016 | Jaeb et al. |
| 2016/0213843 A1 | 7/2016 | Despa et al. |
| 2016/0250398 A1 | 9/2016 | Barr et al. |
| 2016/0271305 A1 | 9/2016 | Kurihara et al. |
| 2016/0287765 A1 | 10/2016 | Canner et al. |
| 2016/0303358 A1 | 10/2016 | Croizat et al. |
| 2017/0189588 A1 | 7/2017 | Croizat et al. |
| 2017/0189666 A1 | 7/2017 | Sealfon et al. |
| 2017/0216501 A1 | 8/2017 | Armstrong et al. |
| 2017/0224975 A1 | 8/2017 | Peer et al. |
| 2017/0296716 A1 | 10/2017 | Middleton et al. |
| 2017/0319758 A1 | 11/2017 | Eddy et al. |
| 2017/0354767 A1 | 12/2017 | Carr et al. |
| 2018/0001000 A1 | 1/2018 | Herwig et al. |
| 2018/0021178 A1 | 1/2018 | Locke et al. |
| 2018/0104391 A1 | 4/2018 | Luxon et al. |
| 2018/0140466 A1 | 5/2018 | Hunt |
| 2018/0250459 A1 | 9/2018 | Kimball et al. |
| 2018/0304065 A1 | 10/2018 | Armstrong et al. |
| 2018/0318476 A1 | 11/2018 | Askem et al. |
| 2018/0333521 A1 | 11/2018 | Hudspeth et al. |
| 2018/0353352 A1 | 12/2018 | Fink et al. |
| 2019/0009008 A1 | 1/2019 | Hartwell |
| 2019/0021541 A1* | 1/2019 | Kuempel ................ A47J 31/36 |
| 2019/0060532 A1 | 2/2019 | Hartwell et al. |
| 2019/0099527 A1 | 4/2019 | Schuessler et al. |
| 2019/0192744 A1 | 6/2019 | Greener et al. |
| 2019/0358372 A1 | 11/2019 | Askem et al. |
| 2020/0121833 A9 | 4/2020 | Askem et al. |
| 2020/0171217 A9 | 6/2020 | Braga et al. |
| 2021/0001022 A1 | 1/2021 | Lin |
| 2021/0077670 A1 | 3/2021 | Long et al. |
| 2021/0392761 A1* | 12/2021 | Kitagawa ............. H05K 5/0213 |

FOREIGN PATENT DOCUMENTS

| | | |
|---|---|---|
| DE | 102010036405 A1 | 1/2012 |
| DE | 102015215165 A1 | 2/2017 |
| EP | 0358302 A2 | 3/1990 |
| EP | 0883430 B1 | 1/2007 |
| EP | 2223711 A1 | 9/2010 |
| EP | 2248546 A2 | 11/2010 |
| EP | 3124059 A1 | 2/2017 |
| EP | 3124060 A1 | 2/2017 |
| FR | 2939320 A1 | 6/2010 |
| GB | 1220857 A | 1/1971 |
| GB | 1415096 A | 11/1975 |
| GB | 2235877 A | 3/1991 |
| GB | 2418738 A | 4/2006 |
| JP | S5647279 U | 4/1981 |
| JP | H01101978 A | 4/1989 |
| JP | H0796029 A | 4/1995 |
| JP | 2000202022 A | 7/2000 |
| JP | 2007218241 A | 8/2007 |
| WO | WO-8700439 A1 | 1/1987 |
| WO | WO-9619335 A1 | 6/1996 |
| WO | WO-03022333 A1 | 3/2003 |
| WO | WO-03053346 A2 | 7/2003 |
| WO | WO-03081762 A1 | 10/2003 |
| WO | WO-2007087808 A1 | 8/2007 |
| WO | WO-2007087809 A1 | 8/2007 |
| WO | WO-2008033788 A2 | 3/2008 |
| WO | WO-2008036344 A1 | 3/2008 |
| WO | WO-2009077722 A1 | 6/2009 |
| WO | WO-2009086580 A1 | 7/2009 |
| WO | WO-2011075706 A1 | 6/2011 |
| WO | WO-2011094410 A2 | 8/2011 |
| WO | WO-2011107972 A1 | 9/2011 |
| WO | WO-2011124388 A1 | 10/2011 |
| WO | WO-2012004298 A1 | 1/2012 |

(56) References Cited

FOREIGN PATENT DOCUMENTS

| | | |
|---|---|---|
| WO | WO-2012009869 A1 | 1/2012 |
| WO | WO-2012027913 A1 | 3/2012 |
| WO | WO-2012027914 A1 | 3/2012 |
| WO | WO-2012027915 A1 | 3/2012 |
| WO | WO-2012027916 A1 | 3/2012 |
| WO | WO-2012100624 A1 | 8/2012 |
| WO | WO-2013015827 A2 | 1/2013 |
| WO | WO-2013029330 A1 | 3/2013 |
| WO | WO-2013063848 A1 | 5/2013 |
| WO | WO-2013064852 A1 | 5/2013 |
| WO | WO-2013126049 A1 | 8/2013 |
| WO | WO-2014115819 A1 | 7/2014 |
| WO | WO-2014164655 A1 | 10/2014 |
| WO | WO-2015091070 A1 | 6/2015 |
| WO | WO-2015197462 A1 | 12/2015 |
| WO | WO-2016103031 A1 | 6/2016 |
| WO | WO-2016109048 A1 | 7/2016 |
| WO | WO-2017044138 A1 | 3/2017 |
| WO | WO-2017062042 A1 | 4/2017 |
| WO | WO-2017160412 A1 | 9/2017 |
| WO | WO-2017197357 A4 | 1/2018 |
| WO | WO-2018009873 A1 | 1/2018 |
| WO | WO-2018009880 A1 | 1/2018 |
| WO | WO-2018041854 A1 | 3/2018 |
| WO | WO-2018150263 A1 | 8/2018 |
| WO | WO-2018150267 A2 | 8/2018 |
| WO | WO-2018167199 A1 | 9/2018 |
| WO | WO-2018185101 A1 | 10/2018 |
| WO | WO-2018195101 A1 | 10/2018 |
| WO | WO-2019063467 A1 | 4/2019 |
| WO | WO-2019129581 A2 | 7/2019 |
| WO | WO-2019139829 A1 | 7/2019 |
| WO | WO-2019179943 A1 | 9/2019 |
| WO | WO-2019211730 A1 | 11/2019 |
| WO | WO-2019211731 A1 | 11/2019 |
| WO | WO-2019211732 A1 | 11/2019 |
| WO | WO-2019224059 A1 | 11/2019 |
| WO | WO-2020011690 A1 | 1/2020 |
| WO | WO-2020120657 A1 | 6/2020 |

OTHER PUBLICATIONS

Hartmann Vivano., "Vivano—Product Application Description," retrieved from http://www.vivanosystem.info/20809.php, accessed on Feb. 28, 2013, 3 pages.

Huntleigh Healthcare, "Negative Pressure Positive Outcomes," WoundASSIST TNP Console and Canister Brochure, 2007, 6 pages.

International Preliminary Report on Patentability for Application No. PCT/EP2020/077478, mailed on Apr. 14, 2022, 9 pages.

International Search Report and Written Opinion for Application No. PCT/EP2020/077478, mailed on Feb. 12, 2021, 15 pages.

Jenkins R.W., et al., "Mechanisms of Resistance to Immune Checkpoint Inhibitors, " British Journal of Cancer, Jan. 2, 2018, vol. 118, https://doi.org/10.1038/bjc.2017.434, pp. 9-16.

KCI, "V.A.C. Freedom User's Guide," May 2002, 16 pages.

Piaggesi A., et al., "SNAP® Wound Care System Made Easy," Wounds International, retrieved from URL: http://www.woundsinternational.com, vol. 3 (1), Feb. 2012, 6 pages.

The Free Dictionary, "Evaporation," The American Heritage®, Science Dictionary, 2005, 3 pages.

Wikipedia, "Battery Charger," retrieved from https://web.archive.org/web/20181109005000/https://en.wikipedia.org/wiki/Battery_charger , on Nov. 9, 2018, 12 pages.

\* cited by examiner

APPARATUSES AND METHODS FOR NEGATIVE PRESSURE WOUND THERAPY

CROSS-REFERENCE TO RELATED APPLICATIONS

This application is a U.S. national stage application of International Patent Application No. PCT/EP2020/077478, filed Oct. 1, 2020, which claims priority to U.K. Provisional Application No. 1914283. 5 filed on Oct. 3, 2019, the disclosure of which is hereby incorporated by reference in its entirety.

BACKGROUND

Field

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and methods of using TNP systems.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy (NPWT), or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema, encouraging blood flow, stimulating the formation of granulation tissue, removing excess exudates and may reduce bacterial load and, thus, infection to the wound. Furthermore, TNP therapy permits less outside disturbance of the wound and promotes more rapid healing.

SUMMARY

Embodiments of the invention disclosed herein are directed to apparatuses, systems, devices and methods for use in negative pressure wound therapy.

In some cases, an apparatus to provide negative pressure to a wound site can comprise a wound dressing configured to be positioned at a wound site, a negative pressure source assembly configured to be in fluid communication with the wound dressing, the negative pressure source assembly comprising a negative pressure source, and a canister configured to receive fluid removed from the wound dressing, the canister comprising an inlet in fluid communication with the wound dressing, an outlet in fluid communication with the negative pressure source, a filter positioned over the outlet, and a shield comprising a plurality of openings and a plurality of protrusions, wherein the plurality of openings are configured to allow air to be drawn from the canister and the plurality of protrusions are configured to protect the filter from components within the interior of the canister. The plurality of protrusions can protrude from a surface of the shield that faces an interior of the canister and extend into the interior of the canister.

The apparatus of the preceding paragraph or any of the apparatuses disclosed herein can include one or more of the following features. The plurality of protrusions can be arranged in rows and columns. A first opening of the plurality of openings can be positioned between a first protrusion and a second protrusion of the plurality of protrusions. One or more of the plurality of protrusions can be between 4-8 mm long. One or more of the plurality of protrusions can be 6 mm long. The plurality of protrusions can comprise a first protrusion and a second protrusion, wherein the first protrusion is between 5-15 mm from the second protrusion. The first protrusion can be between 9-10 mm from the second protrusion. The first protrusion can be 9.5 mm from the second protrusion. The first protrusion can be 10 mm from the second protrusion.

In some cases, an apparatus to provide negative pressure to a wound site can comprise a canister configured to be in fluid communication with a negative pressure source, the canister configured to receive fluid removed from a wound dressing, the canister comprising an inlet in fluid communication with the wound dressing, an outlet in fluid communication with the negative pressure source, a filter positioned over the outlet, and a shield comprising a plurality of openings and a plurality of protrusions, wherein the plurality of openings are configured to allow air to be drawn from the canister and the plurality of protrusions are configured to protect the filter from components within the interior of the canister. The plurality of protrusions can protrude from a surface of the shield that faces an interior of the canister and extend into the interior of the canister.

The apparatus of the preceding paragraph or any of the apparatuses disclosed herein can include one or more of the following features. The plurality of protrusions can be arranged in rows and columns. A first opening of the plurality of openings can be positioned between a first protrusion and a second protrusion of the plurality of protrusions. One or more of the plurality of protrusions can be between 4-8 mm long. One or more of the plurality of protrusions can be 6 mm long. The plurality of protrusions can comprise a first protrusion and a second protrusion, wherein the first protrusion is between 5-15 mm from the second protrusion. The first protrusion can be between 9-10 mm from the second protrusion. The first protrusion can be 9.5 mm from the second protrusion. The first protrusion can be 10 mm from the second protrusion.

In some cases, an apparatus to provide negative pressure to a wound site can comprise a filter configured to be positioned within a canister in fluid communication with a negative pressure source and configured to receive fluid removed from a wound dressing, the filter comprising a first side configured to be adjacent to a fluid outlet of the canister and a second side opposite the first side, wherein the second side faces an interior of the canister, and a shield comprising a plurality of openings and a plurality of protrusions, the shield positioned on the second side of the filter, wherein the plurality of openings are configured to allow air to be drawn from the canister and the plurality of protrusions are configured to protect the filter from components within the interior of the canister. The plurality of protrusions can protrude from a surface of the shield that faces an interior of the canister and extend into the interior of the canister.

The apparatus of the preceding paragraph or any of the apparatuses disclosed herein can include one or more of the following features. The plurality of protrusions can be arranged in rows and columns. A first opening of the plurality of openings can be positioned between a first protrusion and a second protrusion of the plurality of protrusions. One or more of the plurality of protrusions can be between 4-8 mm long. One or more of the plurality of protrusions can be 6 mm long. The plurality of protrusions can comprise a first protrusion and a second protrusion, wherein the first protrusion is between 5-15 mm from the second protrusion. The first protrusion can be between 9-10 mm from the second protrusion. The first protrusion can be 9.5 mm from the second protrusion. The first protrusion can be 10 mm from the second protrusion.

In some cases, an apparatus to provide negative pressure to a wound site can comprise a shield comprising a plurality of openings and a plurality of protrusions, the shield configured to be used within a fluid collection canister in communication with an outlet of the canister, wherein the shield is configured to be used in combination with a filter over the outlet of the canister and the plurality of openings are configured to allow air to be drawn from the canister and the plurality of protrusions are configured to protect the filter from components within the interior of the canister. The plurality of protrusions can protrude from a surface of the shield that faces an interior of the canister and are configured to extend into the interior of the canister.

The apparatus of the preceding paragraph or any of the apparatuses disclosed herein can include one or more of the following features. The canister can be configured to collect fluid removed from a wound dressing positioned over a wound area and under negative pressure. The plurality of protrusions can be arranged in rows and columns. A first opening of the plurality of openings can be positioned between a first protrusion and a second protrusion of the plurality of protrusions. One or more of the plurality of protrusions can be between 4-8 mm long. One or more of the plurality of protrusions can be 6 mm long. The plurality of protrusions can comprise a first protrusion and a second protrusion, wherein the first protrusion is between 5-15 mm from the second protrusion. The first protrusion can be between 9-10 mm from the second protrusion. The first protrusion can be 9.5 mm from the second protrusion. The first protrusion can be 10 mm from the second protrusion.

In some cases, a method of assembling an apparatus for use with negative pressure wound therapy can comprise providing a canister to collect fluid removed from a wound dressing positioned over a wound area, the canister comprising a fluid outlet in communication with a negative pressure source to draw air out of the canister, attaching a filter over the outlet of the canister, the filter comprising a first side configured to be adjacent to the outlet of the canister and a second side opposite the first side, wherein the second side faces an interior of the canister, positioning a shield over the second side of the filter, the shield comprising a plurality of openings and a plurality of protrusions, wherein the plurality of openings are configured to allow air to be drawn from the canister and the plurality of protrusions are configured to protect the filter from components within the interior of the canister. The plurality of protrusions can protrude from a surface of the shield that faces the interior of the canister and extend into the interior of the canister.

Other embodiments of an apparatus to provide negative pressure to a wound site, devices, kits and associated methods are described below.

DETAILED DESCRIPTION

Overview

Embodiments disclosed herein relate to apparatuses, systems, devices and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

Figure 1:
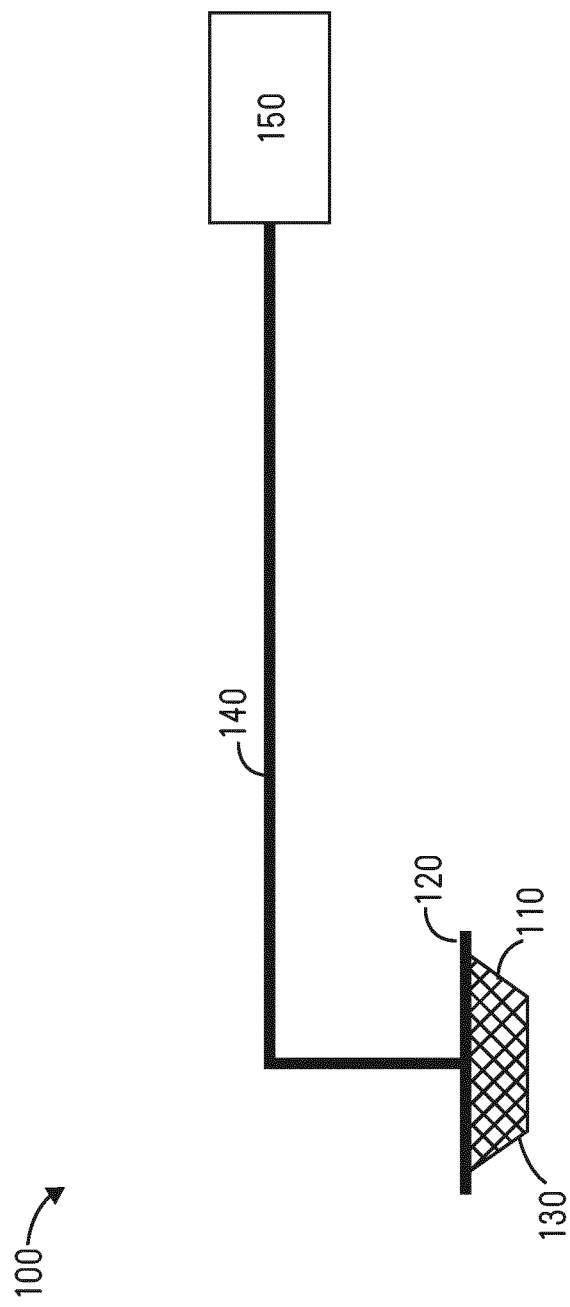
FIG. 1 illustrates a reduced pressure wound therapy system according to some embodiments.

FIG. 1 illustrates an embodiment of a negative or reduced pressure wound treatment (or TNP) system 100 including a wound filler 130 placed inside a wound cavity 110, the wound cavity sealed by a wound cover 120. The wound filler 130 in combination with the wound cover 120 can be referred to as wound dressing. A flow path 140, such as a single or multi lumen tube or conduit, is connected to the wound cover 120 with a negative pressure wound therapy device, for example pump assembly 150, configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110. The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150. In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure setpoints. Low setpoint can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High setpoint can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low setpoint can be delivered for a first-time duration, and upon expiration of the first-time duration, negative pressure at high setpoint can be delivered for a second-time duration. Upon expiration of the second-time duration, negative pressure at low setpoint can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high setpoints and vice versa can be performed according to a step waveform, square waveform, sinusoidal waveform, and the like.

In some embodiments, the TNP system 100 can include multiple wound dressings connected to the pump assembly 150. The performance and wound healing capabilities (such as, fluid management) of the TNP system with multiple wound dressings with the pump assembly 150 can be equivalent to or exceed that of a standard single wound dressing with single pump set-up.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Any of the dressings described herein can be used with Smith and Nephew's Renasys Soft Port connector or interface between the dressing and the pump assembly. For example, the Renasys Soft Port connector can be positioned in the flow path 140 and serve as a port for the wound dressing. In other embodiments, other suitable wound dressings can be utilized.

Pump Assembly and Canister

Figure 2:
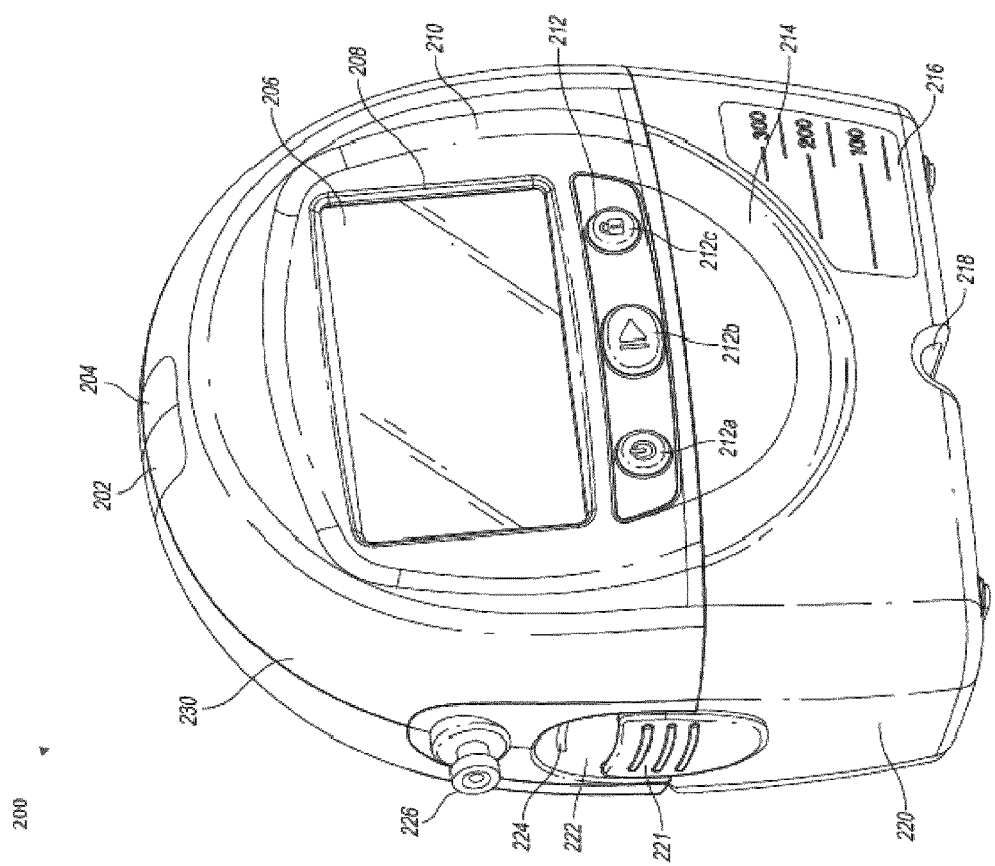
FIG. 2 illustrates a pump assembly and canister according to some embodiments.

FIG. 2 illustrates a front view 200 of a pump assembly 230 and canister 220 according to some embodiments. As is illustrated, the pump assembly 230 and the canister are connected, thereby forming a TNP device or system. The pump assembly 230 includes one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, no flow condition, canister full condition, or any other similar or suitable conditions or combinations thereof. The pump assembly 230 can include additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. As explained herein, the display 206 can be configured to render a number of screens or graphical user interfaces (GUIs) for configuring, controlling, and monitoring the operation of the TNP system. The pump assembly 230 includes a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons 212 configured to allow the user to operate and monitor the operation of the TNP system. As is illustrated, three buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 includes an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various features are omitted or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 includes two latches 221 on the sides of the canister. The exterior of the canister 220 can formed from frosted plastic so that the canister is substantially opaque and the contents of the canister and substantially hidden from plain view. The canister 220 includes a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 includes a tubing channel 218 for connecting to the conduit 140. In some embodiments, one or more of these features, such as the gripping portion 214, are omitted or various additional features are added to the canister 220. Any of the disclosed canisters may include a solidifier.

Electronics and Software

Figure 3:
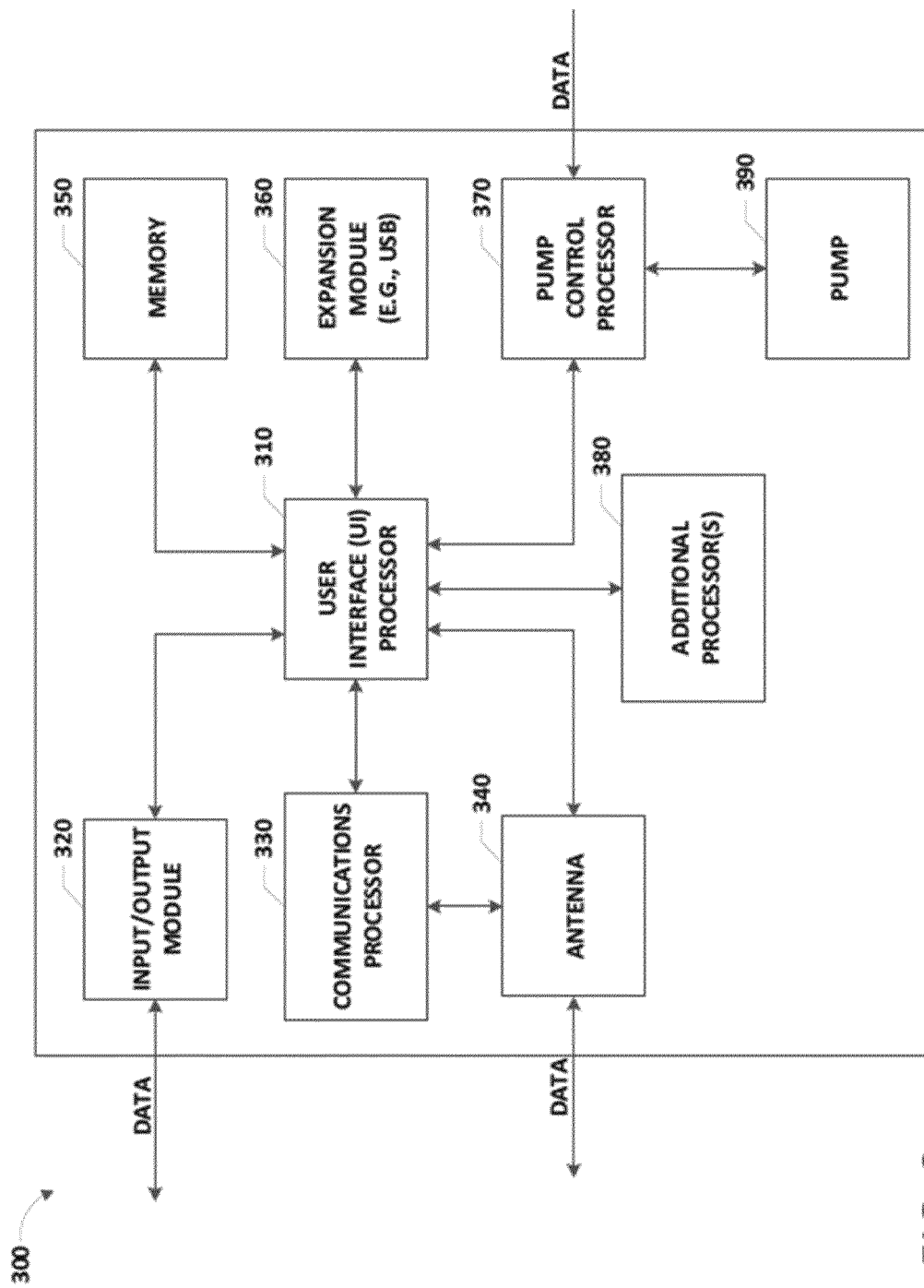
FIG. 3 illustrates an electrical component schematic of a pump assembly according to some embodiments.

FIG. 3 illustrates an electrical component schematic 300 of a pump assembly, such as the pump assembly 230, according to some embodiments. Electrical components can operate to accept user input, provide output to the user, operate the pump assembly and the TNP system, provide network connectivity, and so on. Electrical components can be mounted on one or more printed circuit boards (PCBs). As is illustrated, the pump assembly can include multiple processors. It may be advantageous to utilize multiple processors in order to allocate or assign various tasks to different processors. A first processor can be responsible for user activity and a second processor can be responsible for controlling the pump. This way, the activity of controlling the pump, which may necessitate a higher level of responsiveness (corresponding to higher risk level), can be offloaded to a dedicated processor and, thereby, will not be interrupted by user interface tasks, which may take longer to complete because of interactions with the user.

The pump assembly can include a user interface processor or controller 310 configured to operate one or more components for accepting user input and providing output to the user, such as the display 206, buttons 212, etc. Input to the pump assembly and output from the pump assembly can controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal or external to the processor 310. Any suitable type of memory can be used, including volatile or non-volatile memory, such as RAM, ROM, magnetic memory, solid-state memory, Magnetoresistive random-access memory (MRAM), and the like.

In some embodiments, the processor 310 can be a general-purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (e.g., processor for controlling the display 206, processor for controlling the buttons 212, etc.). The processor 310 can run a suitable operating system, such as a Linux, Windows CE, VxWorks, etc.

The pump control processor 370 can be configured to control the operation of a negative pressure source or pump 390. The pump 390 can be a suitable pump, such as a diaphragm pump, peristaltic pump, rotary pump, rotary vane pump, scroll pump, screw pump, liquid ring pump, pump (for example, diaphragm pump) operated by a piezoelectric transducer, voice coil pump, and the like. The pump control processor 370 can measure pressure in a fluid flow path, using data received from one or more pressure sensors, calculate the rate of fluid flow, and control the pump. The pump control processor 370 can control an actuator, such as a pump motor, so that a desired level of negative pressure is achieved in the wound cavity 110. The desired level of negative pressure can be pressure set or selected by the user. In various embodiments, the pump control processor 370 controls the pump actuator (e.g., pump motor) using pulse-width modulation (PWM). A control signal for driving the pump actuator can be a 0-100% duty cycle PWM signal. The pump control processor 370 can perform flow rate calculations and detect various conditions in a flow path. The pump control processor 370 can communicate information to the processor 310. The pump control processor 370 can include internal memory or can utilize memory 350. The pump control processor 370 can be a low-power processor.

A communications processor 330 can be configured to provide wired or wireless connectivity. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G), Wi-Fi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software or firmware, and the like. The communications processor 330 can provide dual GPS/cellular functionality. Cellular functionality can, for example, be 3G functionality. In such cases, if the GPS module is not able to establish satellite connection due to various factors including atmospheric conditions, building or terrain interference, satellite geometry, and so on, the device location can be determined using the 3G network connection, such as by using cell identification, triangulation, forward link timing, and the like. The pump assembly can include a SIM card, and SIM-based positional information can be obtained.

The communications processor 330 can communicate information to the processor 310. The communications processor 330 can include internal memory or can utilize memory 350. The communications processor 330 can be a low-power processor.

In some embodiments, the pump assembly can track and store various data, such as one or more of positioning data, therapy parameters, logs, device data, and so on. The pump assembly can track and log therapy and other operational data. Data can be stored, for example, in the memory 350.

In some embodiments, using the connectivity provided by the communications processor 330, the device can upload any of the data stored, maintained, or tracked by the pump assembly. For example, the following information can be uploaded to a remote computer or server: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; device location information; patient information; and so on. The device can also download various operational data, such as therapy selection and parameters, firmware and software patches and upgrades, and the like. The pump assembly can provide Internet browsing functionality using one or more browser programs, mail programs, application software (e.g., apps), etc.

In some embodiments, the communications processor 330 can use the antenna 340 to communicate a location of the pump assembly, such as a location of a housing of the pump assembly, to other devices in the proximity (for example, within 10, 20, or 50 meters and the like) of the pump assembly. The communications processor 330 can perform one-way or two-way communication with the other devices depending on the implementation. The communications transmitted by the communications processor 330 can include identifying information to uniquely identify the pump assembly relative to one or more other pump assemblies also in the proximity of the pump assembly. For example, identifying information can include a serial number or a value derived from the serial number. The signal strength of the transmitted communications by the communications processor 330 can be controlled (for example, maintained at a constant or substantially constant level) to enable another device to determine a distance to the pump assembly, such as a distance between the device and the pump assembly.

In some embodiments, the communications processor 330 can communicate with other devices in the proximity of the pump assembly so that the communications processor 330 can itself determine a distance from the pump assembly to the other devices. The communications processor 330, in such embodiments, can track and store the distance from the pump assembly to the other devices or indications of change in the distance over time, and the communications processor 330 can later provide this information to the other devices. For instance, the communications processor 330 can determine a duration of time during which the pump assembly has been removed from a coverage area of a device and subsequently report this time to the device upon being returned to the coverage area.

Flexible Suction Adapter

Figure 4:
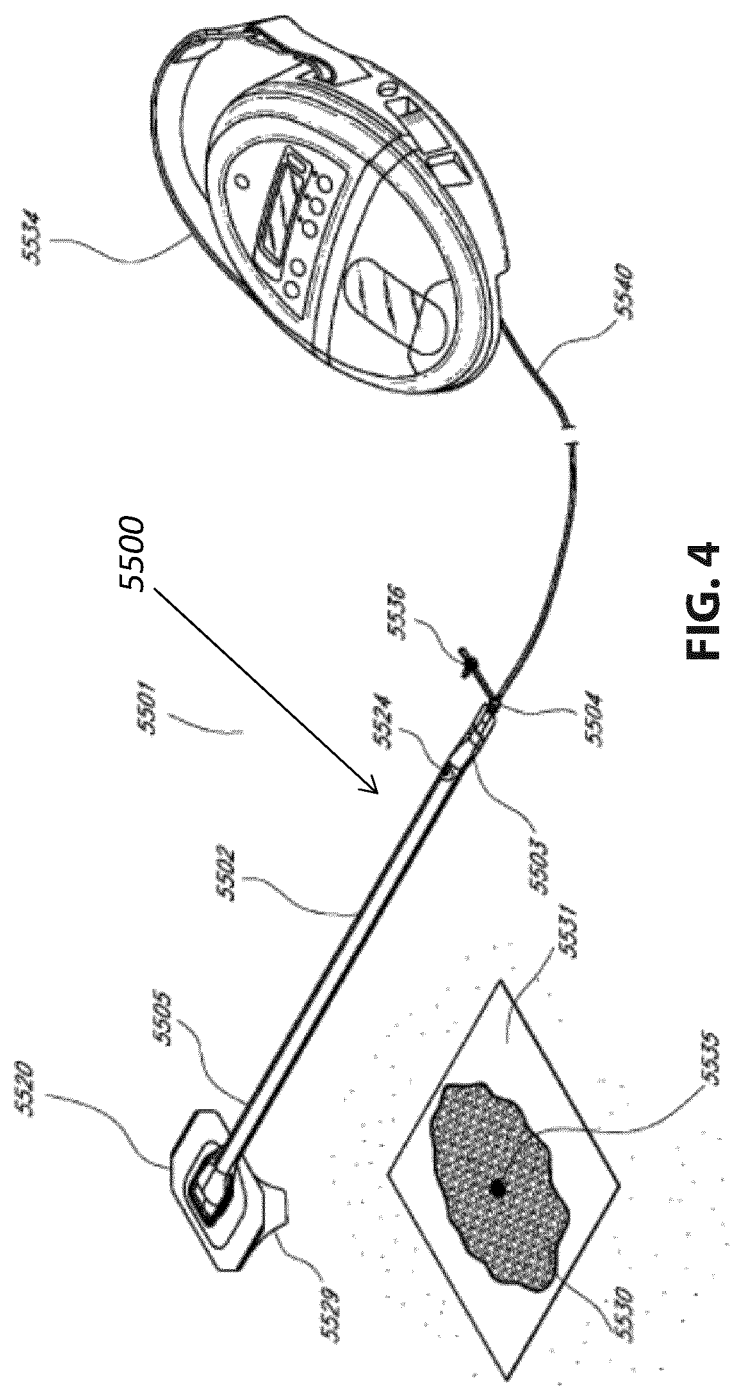
FIG. 4 illustrates an embodiment of a negative pressure wound treatment system comprising a pump, and illustrating a flexible suction adapter being applied to a wound.

FIG. 4 illustrate embodiments of a negative pressure wound treatment system 5501 similar to the embodiment illustrated in FIG. 1. Here, the system 5501 may comprise a flexible suction adapter 5500 having a bridge portion 5502 with a proximal end 5503 and a distal end 5505, and an applicator 5520 at the distal end 5505 of the bridge portion 5502 forming the flexible suction adapter 5500. A connector 5504 is preferably disposed at the proximal end 5503 of the bridge portion 5502, so as to connect to at least one of the channels in the bridge portion. A cap 5536 may be provided with the system 5501 (and can in some cases, as illustrated, be attached to the connector 5504). The cap 5536 can be useful in preventing fluids from leaking out of the proximal end 5503. The system 5501 may include a source of negative pressure such as a pump or negative pressure unit 5534 capable of supplying negative pressure. The pump also preferably comprises a canister or other container for the storage of wound exudates and other fluids that may be removed from the wound. In some embodiments, this pump 5534 may be the pump 200 described in relation to FIG. 2. In some embodiments, this pump 5534 can be a RENASYS GO pump, as sold by Smith & Nephew. The pump 5534 may be connected to the connector 5504 via a tube 5540. In use, the applicator 5520 is placed over an aperture 5535 formed in a drape 5531 that is placed over a suitably-prepared wound 5530, which may in some cases be filled with a wound packing material such as foam or gauze. Subsequently, with the pump 5534 connected via the tube 5540 to the connector 5504, the pump is activated, thereby supplying negative pressure to the wound. Application of negative pressure may be applied until a desired level of healing of the wound 5530 is achieved.

In use, and with reference to FIG. 4, the system 5501 may be used in a similar fashion to the other embodiments previously disclosed herein, such as the system 100 described in relation to FIG. 1. A wound site 5530 is preferably cleaned and prepared in a suitable fashion, and a wound packing material, if necessary, placed into the wound site, followed by a drape 5531. An aperture 5535 through the drape to the wound site is then created, although some embodiments may have a pre-made aperture 5535. Subsequently, an operator may situate the applicator portion 5520 over the aperture 5535. After removing the backing layer 5529 (if present) from the adhesive layer on the underside of the applicator portion 5520, the applicator is sealed to the drape 5531, and the backing layer 5552 (if present) is also removed from the applicator portion 5520. A fluidic conduit such as a tube 5540 may then be connected to the connector 5504. The tube 5540 may also be connected to connector 5504 prior to applying the applicator to the wound site. The fluidic conduit is connected to a source of negative pressure 5534, preferably with a container suitable for containing wound exudate interposed therebetween. The application of negative pressure may then be effectuated to the wound site 5530 until the wound site progresses to a desired level of healing.

During use of the system 5501, wound exudate from the wound site 5530 is drawn by the negative pressure through the bridge portion 5502. The negative pressure draws air passing through the bridge portion 5502 back toward the source of negative pressure or pump. In some embodiments, the controlled air leak 5524 provides a constant flow of air through the suction adapter 5500, which then may be used to determine whether blockage or leakage is present. Causes of blockage can include, for example, situations where a portion of the bridge portion 5502 becomes occluded with wound debris. Leakage causes can include, for example, improper sealing of the drape over the wound site, or physical damage to the suction adapter 5500 leading to excess air leaking into the system. The blockage or leakage may be determined, in certain embodiments, by measuring the speed of the pump while the pump works to maintain a constant negative pressure. Pump speed may also be measured indirectly by measuring the amount of voltage or signal sent to the pump.

Filter Accessory

The system can include a source of negative pressure such as a pump or negative pressure unit 5534 as illustrated in FIG. 4 capable of supplying negative pressure. The system can also preferably comprise a canister or other container for the storage of wound exudates and other fluids that may be removed from the wound.

Figure 5A:
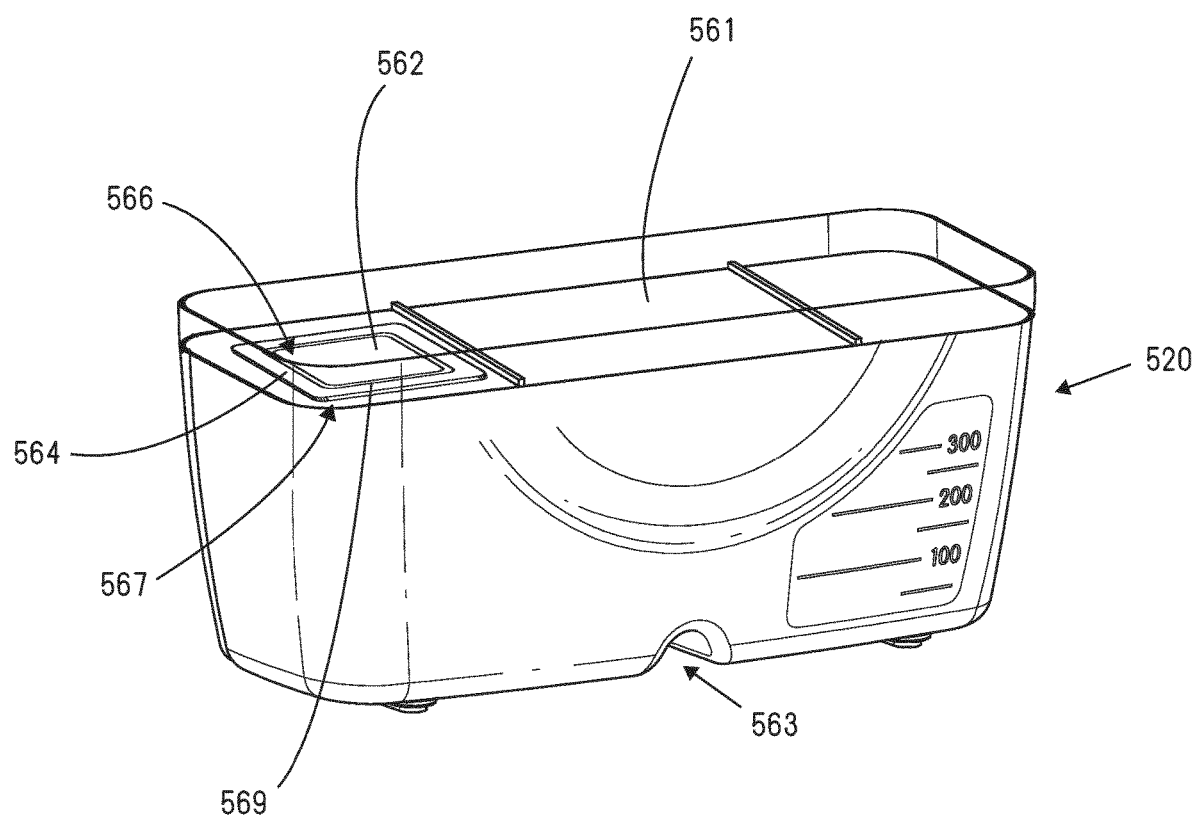
FIGS. 5A-5C illustrate embodiments of a negative pressure wound treatment system comprising a pump assembly and a canister.
Figure 5B:
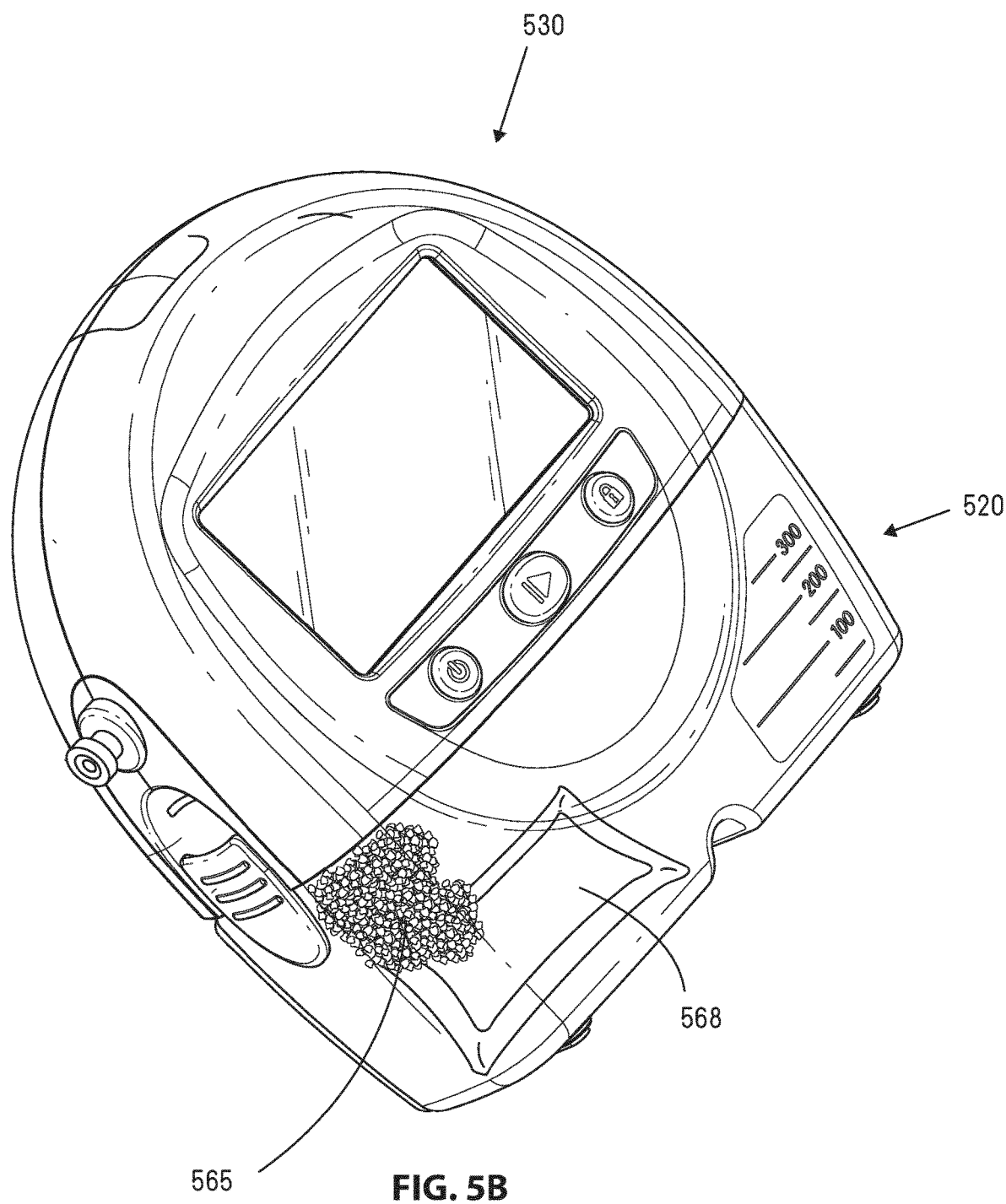
Figure 5C:
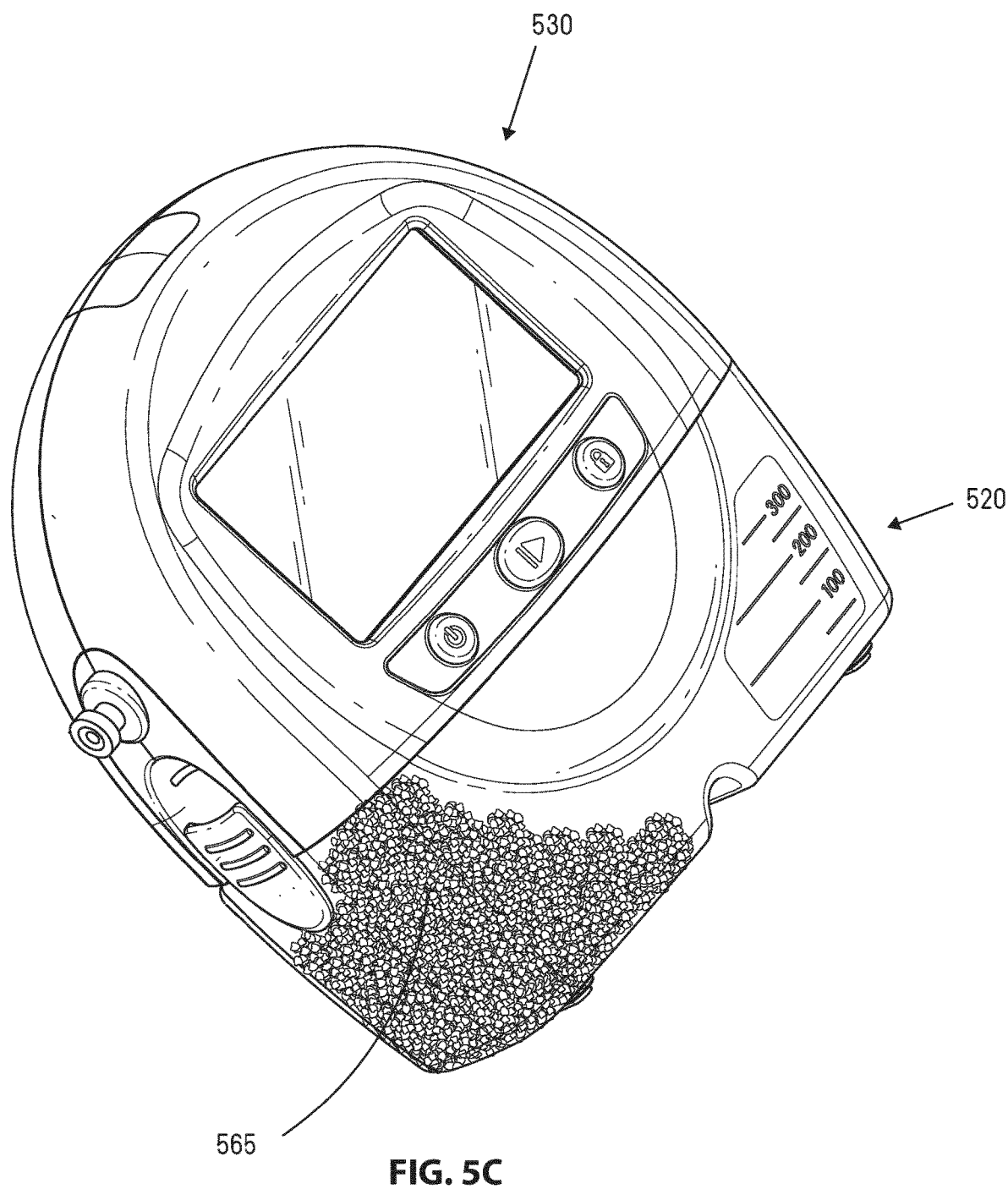

FIGS. 5A-5C illustrate embodiments of a pump assembly and a canister for use with a wound dressing of a negative pressure wound treatment system. FIG. 5A illustrates a top perspective view of the canister with the pump assembly removed. The pump assembly can include a negative pressure source as described herein. The canister 520 and the pump assembly 530 can be similar to the canister 220 and pump assembly 230 described with reference to FIG. 2 previously. As shown in FIG. 5A, the canister 520 can include a top portion 561 that is configured to connect to a pump assembly 530. The canister 520 can be configured to receive fluid removed from the wound dressing. The canister 520 can include an inlet 563 in fluid communication with the wound dressing and an outlet 562 in fluid communication with the negative pressure source within the pump assembly 530. This allows negative pressure wound therapy to be delivered to the wound whilst emptying exudate from the wound site into the canister. As shown in FIG. 5A, the canister for use with the negative pressure pump can have a weld area or filter area 569 that covers and extends around the outlet 562 with a filter 564 positioned over the outlet. As the air is drawn out of the outlet, the air passes through the filter 564. The filter 564 can be positioned on the top portion of the canister covering the outlet 562 as shown in FIG. 5A. The filter 564 can be positioned between the outlet 562 and an inlet (not shown) on the pump assembly 530 that is in fluid communication with the negative pressure source.

FIGS. 5B-5C illustrate an embodiment of the canister 520 attached to the pump assembly 530. The canister can include a fluid solidifier 565 within the interior chamber of the canister. In some cases, the fluid solidifier can include superabsorbent particles. For example, the canister can contain a super absorbent polymers (SAP) bag 568 which can contain a fluid solidifier 565. When the fluid solidifier is contained in a bag or pouch, the bag or pouch can be constructed to release the fluid solidifier as exudate is collected in the canister and the exudate comes into contact with the bag or pouch. The fluid solidifier 565 can consolidate the exudate that is collected in the canister. When the canister 520 fills with exudate the fluid solidifier 565 can absorb the fluid within the canister. As the fluid solidifier 565 absorbs fluid, the fluid solidifier 565 can expand and at least partially fill the canister 520 as shown in FIG. 5C. As used herein, when the fluid solidifier begins to absorb fluid and swell, the fluid solidifier is referred to as activating or being activated.

As the fluid solidifier expands, the area around the filter of the canister can become blocked and air can be restricted from passing through the filter. The blockage can be even more restrictive if the fluid solidifier 565 becomes activated on or around the filter area. The activation of the fluid solidifier 565 at or near the filter area can block air from being drawn from the outlet and/or filter of the canister. In use, if the canister is full, an alarm can be triggered to alert the user to empty or change the canister. For example, if the filter area of the canister is blocked off or blocked by fluid, a canister blockage alarm can be triggered indicating that the canister is full. However, in cases where the filter area is blocked by the fluid solidifier 565 activating at or near the filter area air cannot be drawn from the outlet and/or filter of the canister. This blockage of air can cause the system to trigger a false blockage alarm.

Figure 6A:
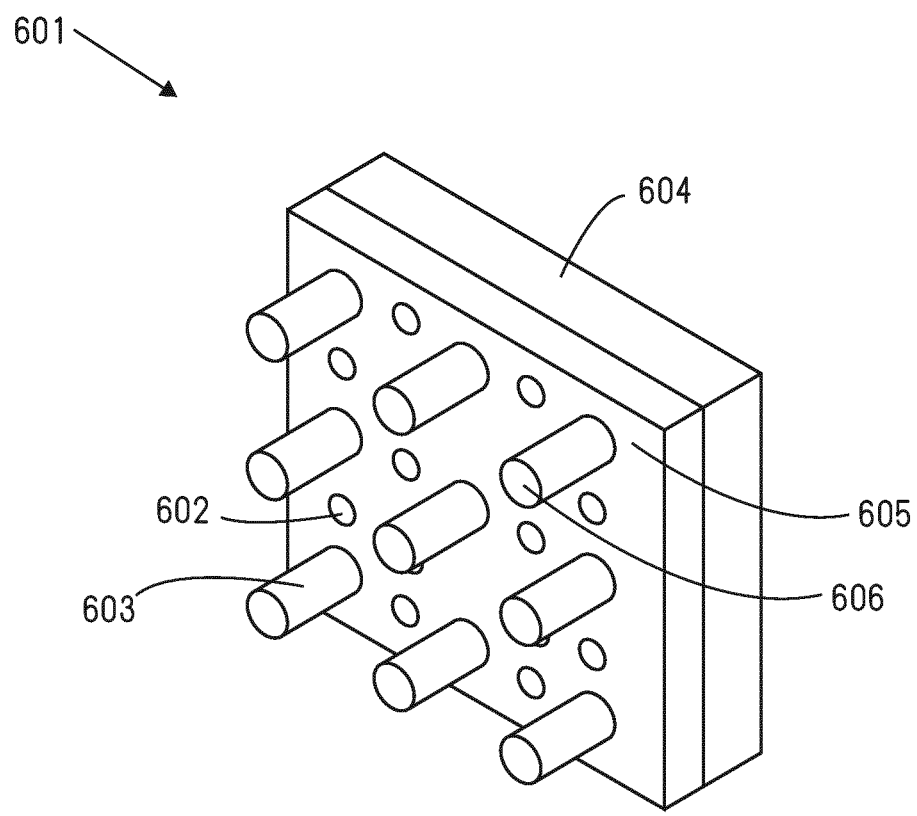
FIGS. 6A-6C and 7 illustrate embodiments of filter accessory for use with a negative pressure wound treatment system.
Figure 6B:
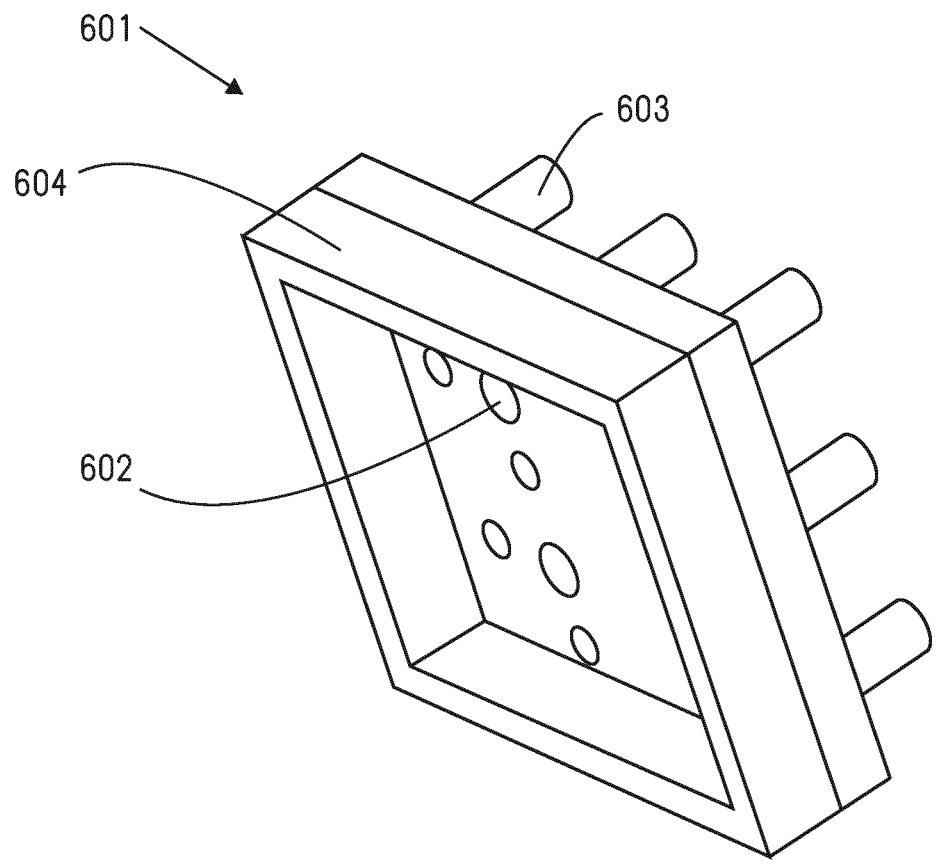
Figure 6C:
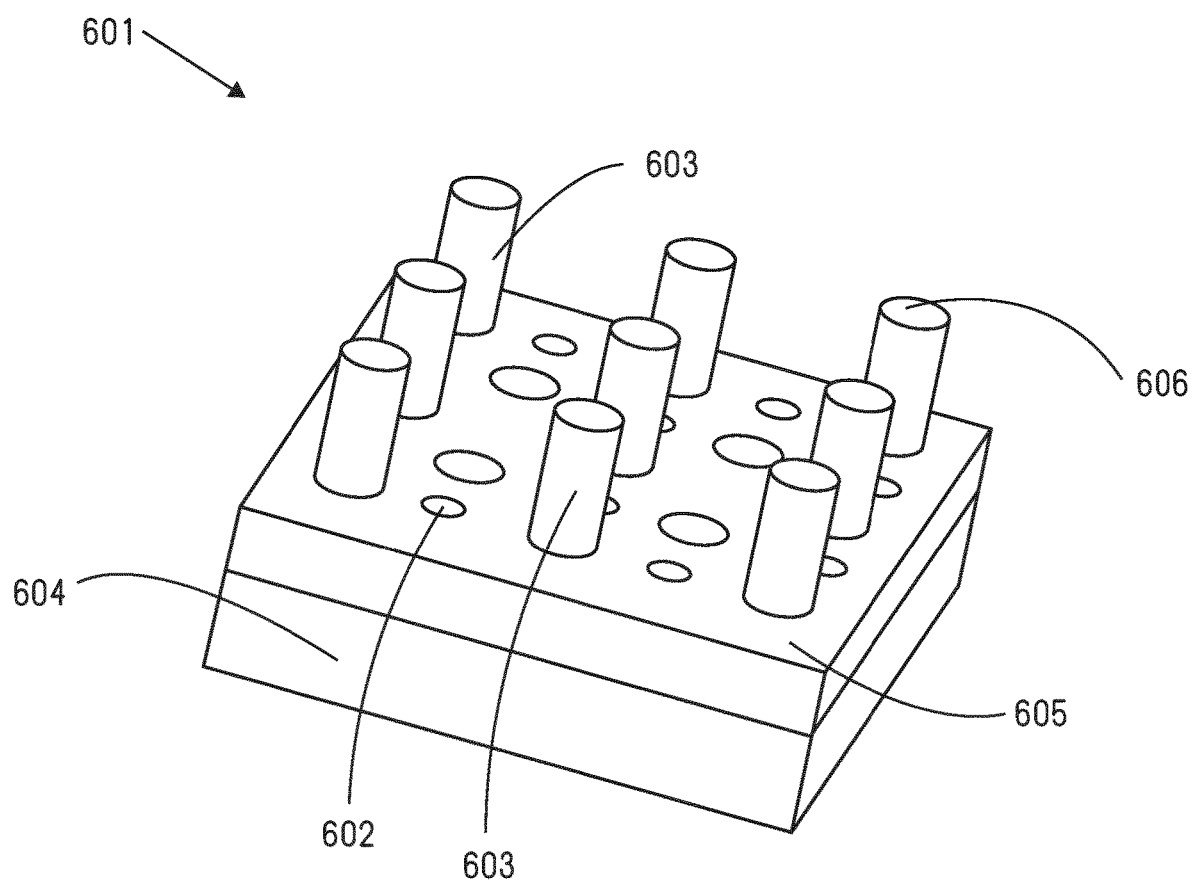

A filter assembly can be used that provides a shield 601 over the filter to prevent the fluid outlet and/or filter from being covered, blocked, or clogged with the fluid solidifier or other substance in the canister. The shield can have a plurality of openings 602 and a plurality of protrusions 603 as illustrated in FIGS. 6A-6C. The plurality of openings 602 are configured to allow air to be drawn from the canister and the plurality of protrusions 603 are configured to protect the filter from components within the interior of the canister. In some cases, the protrusions can be pins, ribs, bumps, or any other structure protruding from the surface of the shield that faces the interior of the canister.

Protrusions of varying geometries and sizes can be used. For example, circular columns, square columns, hexagonal columns, and/or columns of any shape may be used. In some cases, the protrusions can be truncated in shape or have tapered side walls. The filter can have a first side 566 that is adjacent to and/or covering the outlet of the canister and an opposite second side 567 that is facing the interior of the canister as illustrated in FIG. 5A. The shield can be positioned on the second side of the filter between the interior of the canister and the filter. The shield can have any configuration of openings and protrusions. The openings 602 can allow air to be drawn and the protrusions 603 can prevent a substance in the canister from covering or blocking the filter area. For example, the protrusions 603 can prevent the fluid solidifier from being activated on the filter area. In some cases, if a fluid solidifier or other substance does cover the filter area when the shield is present, the protrusions 603 can prevent the fluid solidifier or other substance from fully covering or blocking the filter area and causing a "false" blockage alert.

In some cases, the filter and the shield can be provided as one integral unit that is placed within the canister. In other cases, the filter and shield can be provided separately. For example, the filter can be configured within the canister and the shield can be placed over the filter. In some cases, a canister can be retrofitted with the filter and shield. For example, a canister can be provided with or without a filter covering an outlet. The shield can be positioned on the second side (side facing the interior of the canister) of the filter with the protrusions extending into the interior of the canister.

In some cases, an apparatus can be assembled with the filter and shield for use with negative pressure wound therapy. A canister can be provided to collect fluid removed from a wound dressing positioned over a wound area. The canister can include a fluid outlet in communication with a negative pressure source to draw air out of the canister. A filter can be attached over the outlet of the canister. The filter can include a first side configured to be adjacent to the outlet of the canister and a second side opposite the first side and facing an interior of the canister as described herein. A shield can be positioned over the second side of the filter. The shield can include the plurality of openings and plurality of protrusions. The plurality of openings can allow air to be drawn from the canister and the plurality of protrusions can protect the filter from components within the interior of the canister. If the canister is being assembled with a separate lid or top section (which the filter and the shield are attached to), the lid or top portion can be attached to or placed over the opening in the canister body enclosing the canister interior.

In some cases, the shield can be used with a support structure 604 which increases the thickness of the shield. The support structure 604 can raise the shield with the openings and protrusions a certain distance from the filter. As illustrated in FIGS. 6A-6C, the support structure 604 can be positioned between the filter and the shield. In some cases, the support structure can have a height of 1.5 mm (about 1.5 mm). The support structure can have a height of less than 1.5 mm, between 1.5 mm to 6 mm (about 1.5 mm to about 6 mm), or more than 6 mm. In some cases, the shield can be manufactured with the support structure or the support structure and shield can be provided separately and combined before positioning over the filter within the canister or combined during assembly over the filter. As illustrated in FIG. 6B, the support structure 604 can be a rectangular frame structure that supports the outer perimeter of the shield with an opening in the middle of the frame area that allows fluid to pass through.

The shield can also allow the canister to be used in any orientation. For example, the shield can protect the filter area from being blocked or covered by a fluid solidifier or other substance when the canister is turned, tilted, or tipped in any orientation. This also allows the canister to be used in any orientation without triggering a "false" blockage alert.

In some cases, the systems and apparatus described herein can provide negative pressure to a wound site. The apparatus can include a wound dressing that can be positioned at the wound site and a negative pressure source assembly can be in fluid communication with the wound dressing. The negative pressure assembly can include a negative pressure source and a canister that can receive fluid removed from the wound dressing. The canister can include an inlet in fluid communication with the wound dressing, an outlet in fluid communication with the negative pressure source, a filter positioned over the outlet and a shield comprising a plurality of openings and a plurality of protrusions, wherein the plurality of openings are configured to allow air to be drawn from the canister and the plurality of protrusions are configured to protect the filter from components within the interior of the canister.

The shield can have one or more protrusions on the canister facing surface of the shield and one or more openings passing through the shield. In some cases, the orientation and number of the protrusions and openings can vary. As illustrated in FIG. 6A-6C, the shield can have nine protrusions 603 and 14 openings. In other cases, six protrusions and 12 openings can be used. In some cases, the plurality of protrusions can be arranged in rows and columns. In some cases, the plurality of protrusions can be distributed randomly on the shield.

In some cases, the height of the protrusions can be between 4 mm to 13 mm (about 4 mm to about 13 mm). The height of the protrusions can be 6 mm (about 6 mm). In some cases, one or more of the plurality of pins is between 4-8 mm long. In some cases, one or more of the plurality of pins is 6 mm long. As used herein, the height or length of the protrusions can be used interchangeably to refer to the distance between the proximal end of the protrusion connected to the surface of the shield and the distal most end of the protrusion. As used herein, the height or length of the protrusion can be measured from the surface of the shield 605 to the distal most end 606 of the protrusion as shown in FIG. 6A.

In some cases, an opening of the plurality of openings can be positioned between a first protrusion and a second protrusion of the plurality of protrusions. In some cases, the openings of the plurality of openings can be distributed randomly on the shield or can be arranged in rows or columns. In some cases, the openings can be of varying sizes as illustrated in FIGS. 6A-6C.

Figure 7:
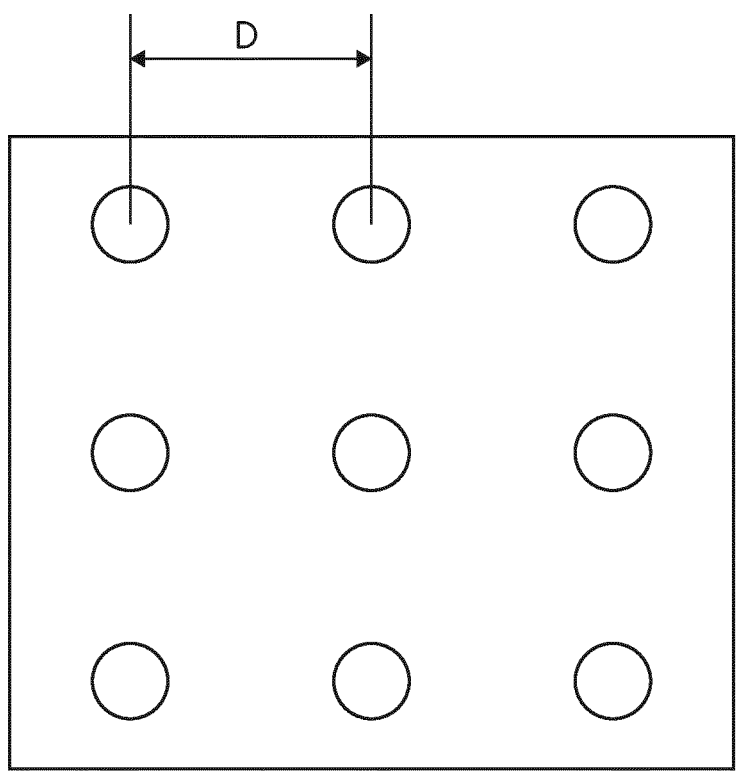

FIG. 7 illustrates a filter shield shown without the openings. FIG. 7 illustrates an embodiment of the filter shield illustrating the distance D between the protrusions of the filter shield. In some cases, the protrusions can be separated by 5 mm to 15 mm (about 5 mm to about 15 mm). In some cases, the distance between any two protrusions of the plurality of protrusions can be 9.5 mm (about 9.5 mm). In some cases, the distance between any two protrusions of the plurality of protrusions can be 10 mm (about 10 mm). The distance between any two protrusions of the plurality of protrusions can vary. The distance between all protrusions can be the same or about the same. In other cases, the distance between the protrusions can vary and the protrusions are not evenly distributed on the shield. For example, the distance between any two protrusions can be different from the distance between any other two protrusions. As used herein, the distance between any two protrusions can be measured from the center point of a first protraction to the center point of a second protrusion as illustrated in FIG. 7.

For example, the plurality of protrusions comprises a first protrusion and a second protrusion, wherein the first protrusion is a distance D from the second protrusion. In some cases, the first protrusion is between 5-15 mm (about 5-15 mm) from the second protrusion. In some cases, the first protrusion can be between 9-10 mm (about 9-10 mm) from the second protrusion. In some cases, the first protrusion can be 9.5 mm from the second protrusion. In some cases, the first protrusion can be 10 mm from the second protrusion.

In some cases, the protrusions can prevent the fluid solidifier or other substance from collapsing on the openings in the shield and negative pressure can be drawn through the openings. In some cases, a portion of the fluid solidifier or other substance may get between some protrusions or may be positioned over the protrusions of the shield but at least some of the openings remain unobstructed and negative pressure can still be drawn through the unobstructed openings. In some cases, the shield can allow the patient more mobility while using the canister. By preventing blockage of the filter, the shield can allow the canister to be tipped, tilted, or otherwise moved without obstructing the filter or filter shield. This can allow for the patient to be active or mobile while using the device.

Figure 8A:
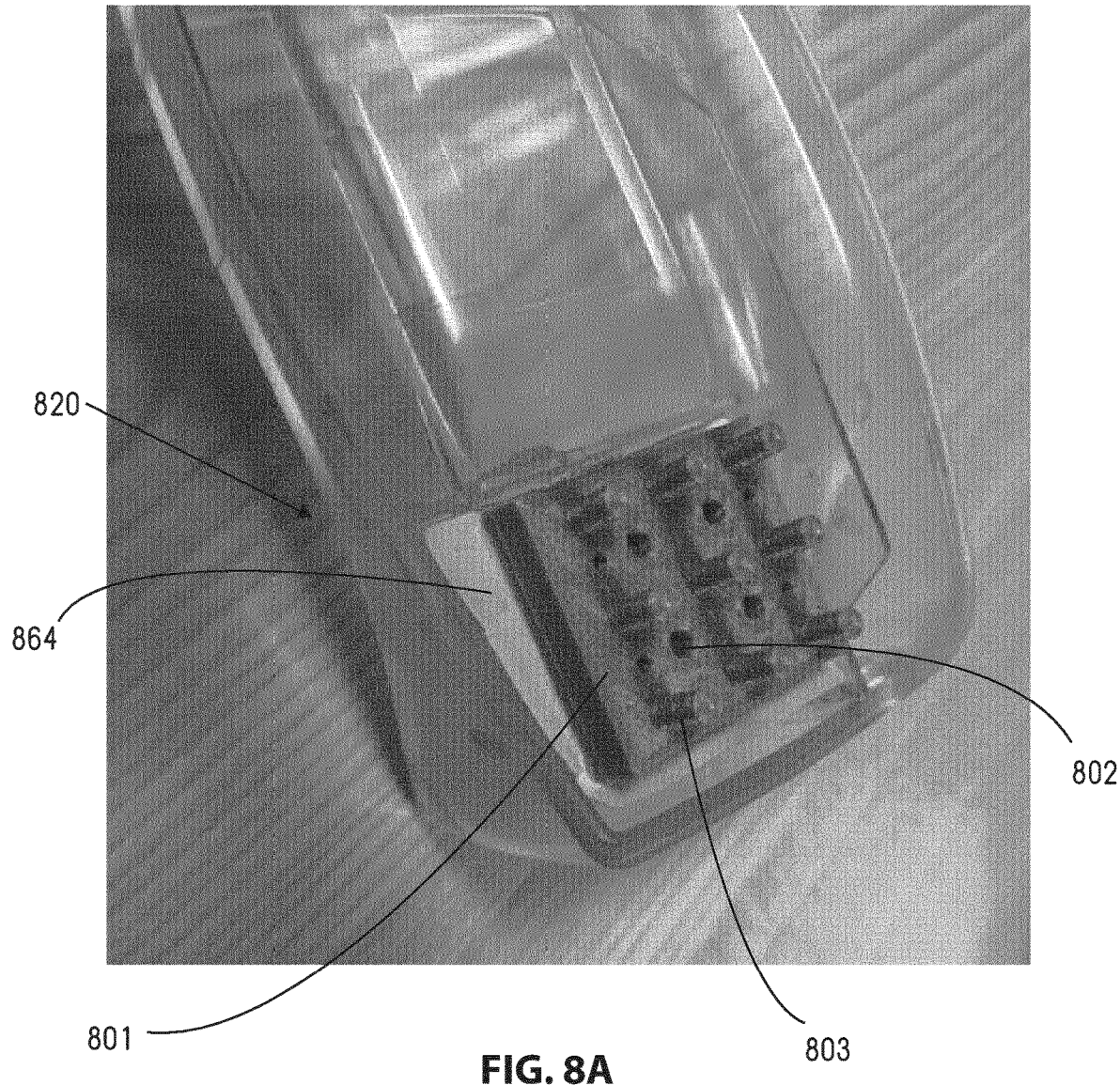
FIGS. 8A-8B illustrate embodiments of a canister with a filter accessory.
Figure 8B:
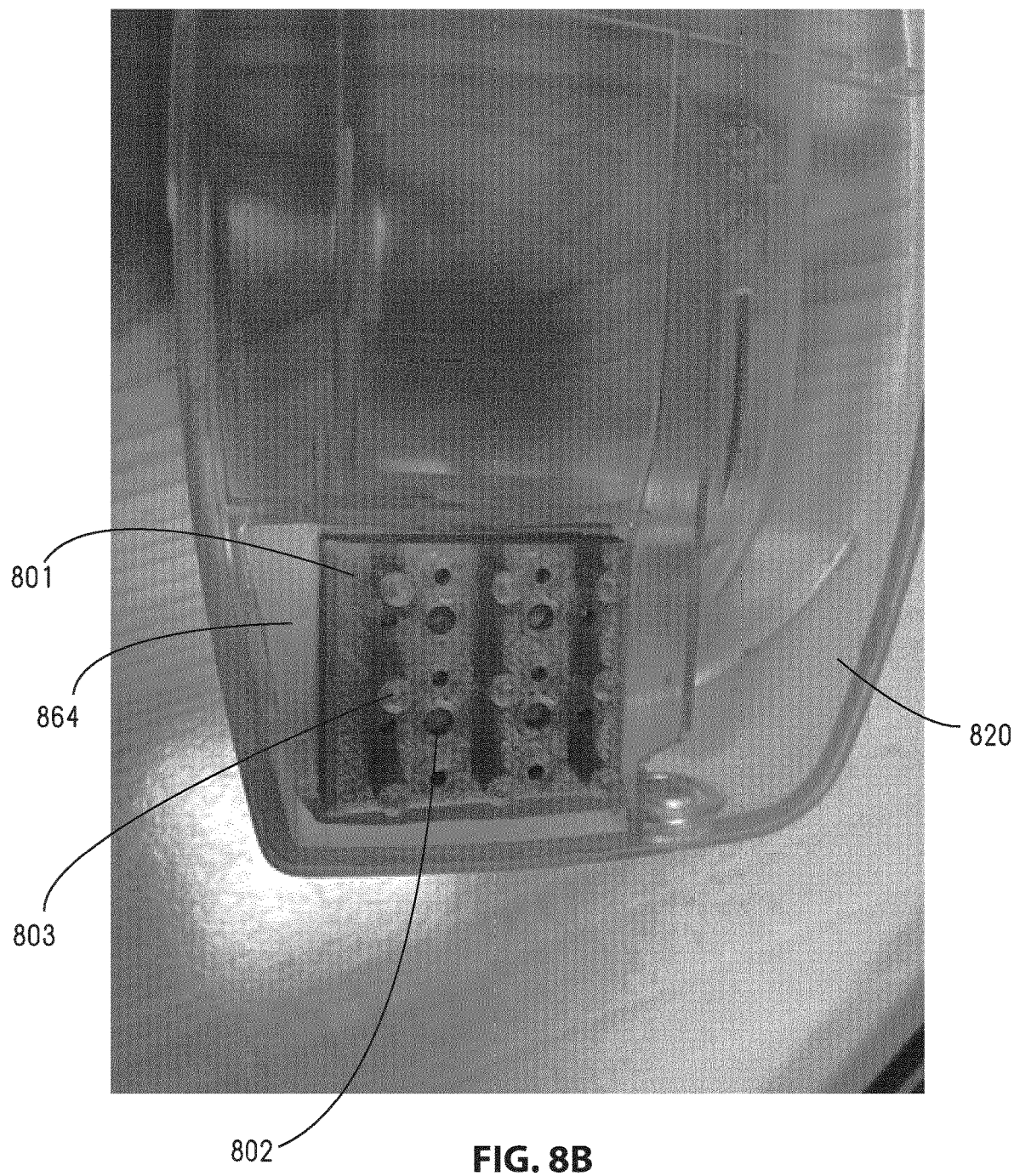

In some cases, the shield can prevent the fluid solidifier from triggering a false alarm. As the canister continues to fill with exudate collected form the wound the fluid solidifier can become more saturated. Once there is enough fluid collected, the fluid solidifier can become fully saturated and free fluid can exist in the canister. The free fluid can then block the filter and shield component triggering the canister full alarm and correctly signaling that the canister is full. FIGS. 8A-8B illustrate embodiments of a canister with a filter accessory. The canister 820 is similar to the canister 520 described with reference to FIGS. 5A-5C. FIGS. 8A-8B show a bottom view of the top portion of the canister (the portion of the canister top that faces the interior of the canister when assembled) with a filter 864 and a filter shield 801. Similar to the filter 564 described with reference to FIG. 5A, the filter 864 can be positioned over an outlet in the canister that is in communication with an inlet to the pump assembly so that air is drawn through the filter prior to exiting the canister. The shield 801 can be similar to the shield 601 described with reference to FIGS. 6A-6C. The shield 801 can be positioned over the filter with protrusions 803 extending in to the interior of the canister when assembled and openings 802 configured to allow fluid to pass through. As shown in FIGS. 8A-8B, the shield 801 can be positioned on a second side of the filter that faces the interior fluid collecting chamber of the canister. Accordingly, the shield 801 can be positioned between the filter 864 and the interior of the canister.

Figure 9A:
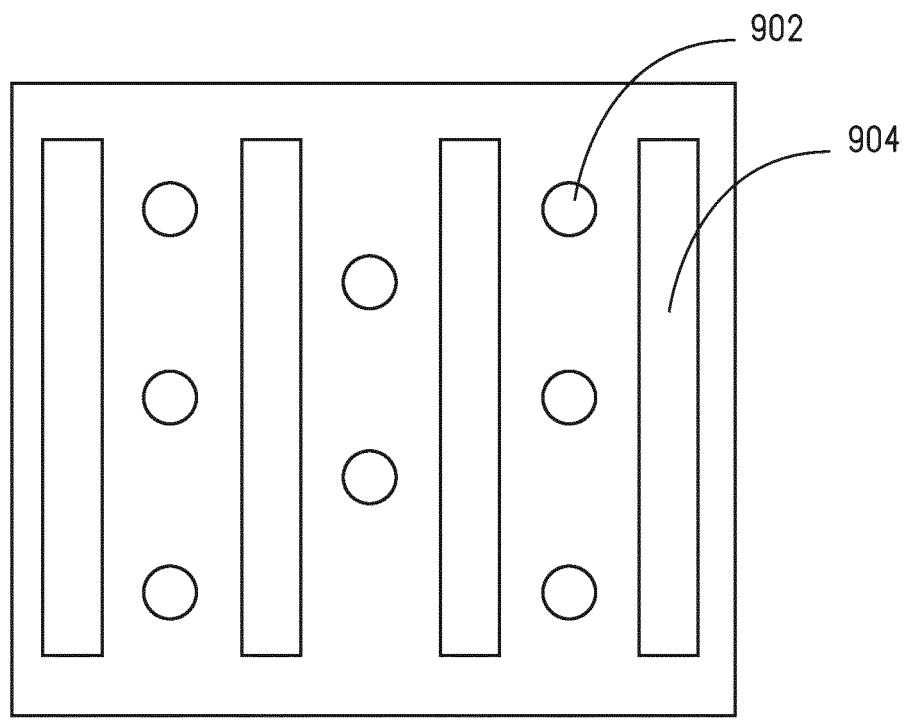
FIGS. 9A-9B illustrate embodiments of a filter accessory for use with a negative pressure wound treatment system.
Figure 9B:
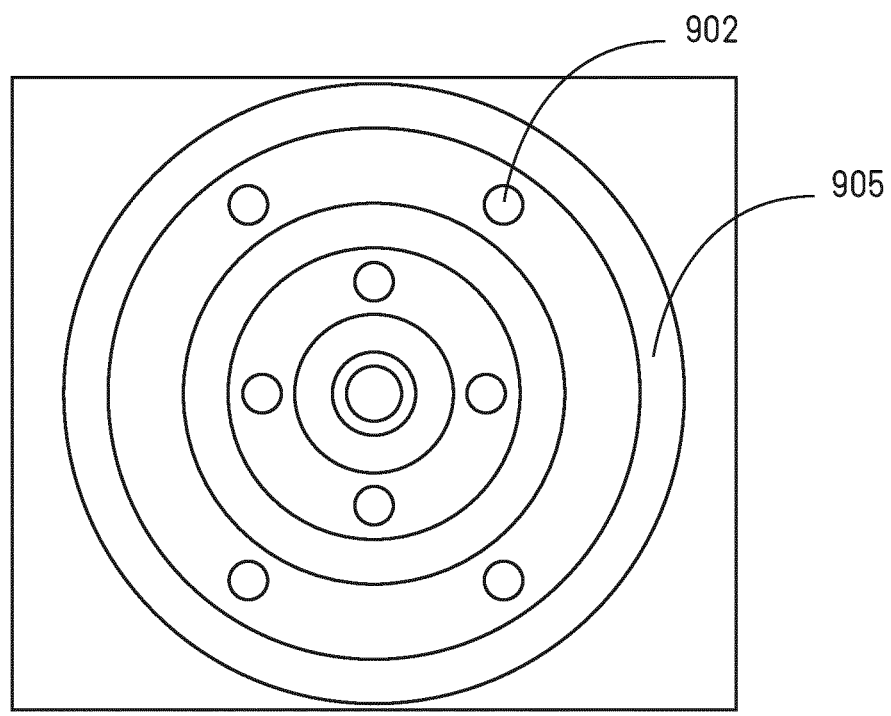

Other geometries of protrusions can be used. Parallel or substantially parallel ribs or concentric or substantially concentric rings can be used with openings in the channels between the ribs or rings to prevent the fluid outlet from being covered, blocked, or clogged with the fluid solidifier or other substance in the canister. FIG. 9A illustrates an embodiment of a shield with protrusions that are parallel or substantially parallel ribs 904 and openings 902 in the channels between the ribs. FIG. 9B illustrates an embodiment of a shield with protrusions that are concentric or substantially concentric rings 905 and openings 902 in the channels between the rings. FIGS. 9A-9B illustrate the interior facing surface of the shield. The ribs 904 or rings 905 can be extend from the surface of the shield into the canister as described with reference to the protrusions 603 described with reference to FIGS. 6A-6C. In some cases, the height of the ribs or rings can be between 4 mm to 13 mm (about 4 mm to about 13 mm).

Terminology

Depending on the embodiment, certain operations, acts, events, or functions of any of the processes described herein can be performed in a different sequence, can be added, merged, or left out altogether (such as not all are necessary for the practice of the processes). Moreover, in certain embodiments, operations, acts, functions, or events can be performed concurrently, such as through multi-threaded processing, interrupt processing, or multiple processors or processor cores or on other parallel architectures, rather than sequentially.

The processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices. Likewise, the data repositories shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Any patents and applications and other references noted above, including any that may be listed in accompanying filing papers, are incorporated herein by reference. Aspects of the disclosure can be modified, if necessary, to employ the systems, functions, and concepts of the various references described herein to provide yet further implementations.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Any of the embodiments described herein can be used with a canister or without a canister. Any of the dressing embodiments described herein can absorb and store wound exudate.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

What is claimed is:

1. An apparatus to provide negative pressure to a wound site comprising:
  a wound dressing configured to be positioned at a wound site;
  a negative pressure source assembly configured to be in fluid communication with the wound dressing, the negative pressure source assembly comprising;
    a negative pressure source; and a canister configured to receive fluid removed from the wound dressing, the canister comprising:
an inlet in fluid communication with the wound dressing;
an outlet in fluid communication with the negative pressure source;
a filter positioned over the outlet;
a shield comprising a plurality of openings and a plurality of protrusions, wherein the plurality of openings are configured to allow air to be drawn from the canister and the plurality of protrusions protrude from a surface of the shield that faces an interior of the canister and extend into the interior of the canister, the plurality of protrusions are configured to protect the filter from components within the interior of the canister, and
wherein the plurality of protrusions are freestanding projections that protrude from a surface of the shield that faces an interior of the canister and the freestanding projections extend into the interior of the canister.

2. The apparatus according to claim 1, wherein the plurality of protrusions are arranged in rows and columns.

3. The apparatus according to claim 1, wherein a first opening of the plurality of openings is positioned between a first protrusion and a second protrusion of the plurality of protrusions.

4. The apparatus according to claim 1, wherein one or more of the plurality of protrusions is between 4-8 mm long.

5. The apparatus according to claim 4, wherein one or more of the plurality of protrusions is 6 mm long.

6. The apparatus according to claim 1, wherein the plurality of protrusions comprises a first protrusion and a second protrusion, wherein the first protrusion is between 5-15 mm from the second protrusion.

7. The apparatus according to claim 6, wherein the first protrusion is between 9-10 mm from the second protrusion.

8. The apparatus according to claim 6, wherein the first protrusion is 9.5 mm from the second protrusion.

9. The apparatus according to claim 6, wherein the first protrusion is 10 mm from the second protrusion.

10. An apparatus to provide negative pressure to a wound site comprising:
a canister configured to be in fluid communication with a negative pressure source, the canister configured to receive fluid removed from a wound dressing, the canister comprising:
an inlet in fluid communication with the wound dressing;
an outlet in fluid communication with the negative pressure source;
a filter positioned over the outlet;
a shield comprising a plurality of openings and a plurality of protrusions, wherein the plurality of openings are configured to allow air to be drawn from the canister and the plurality of protrusions protrude from a surface of the shield that faces an interior of the canister and extend into the interior of the canister, the plurality of protrusions are configured to protect the filter from components within the interior of the canister, and
wherein the plurality of protrusions are freestanding projections that protrude from a surface of the shield that faces an interior of the canister and the freestanding projections extend into the interior of the canister.

11. The apparatus according to claim 10, wherein the plurality of protrusions are arranged in rows and columns.

12. The apparatus according to claim 10, wherein a first opening of the plurality of openings is positioned between a first protrusion and a second protrusion of the plurality of protrusions.

13. The apparatus according to claim 10, wherein one or more of the plurality of protrusions is between 4-8 mm long.

14. The apparatus according to claim 13, wherein one or more of the plurality of protrusions is 6 mm long.

15. The apparatus according to claim 10, wherein the plurality of protrusions comprises a first protrusion and a second protrusion, wherein the first protrusion is between 5-15 mm from the second protrusion.

16. The apparatus according to claim 15, wherein the first protrusion is between 9-10 mm from the second protrusion.

17. The apparatus according to claim 15, wherein the first protrusion is 9.5 mm from the second protrusion.

18. The apparatus according to claim 15, wherein the first protrusion is 10 mm from the second protrusion.

19. A method of assembling an apparatus for use with negative pressure wound therapy, the method comprising:
providing a canister configured to collect fluid removed from a wound dressing positioned over a wound area, the canister comprising a fluid outlet in communication with a negative pressure source to draw air out of the canister;
attaching a filter over the outlet of the canister, the filter comprising a first side configured to be adjacent to the outlet of the canister and a second side opposite the first side, wherein the second side faces an interior of the canister;
positioning a shield over the second side of the filter, the shield comprising a plurality of openings and protrusions, wherein the plurality of openings are configured to allow air to be drawn from the canister and the plurality of protrusions protrude from a surface of the shield that faces the interior of the canister and extend into the interior of the canister, the plurality of protrusions are configured to protect the filter from components within the interior of the canister, and
wherein the plurality of protrusions are freestanding projections that protrude from a surface of the shield that faces an interior of the canister and the freestanding projections extend into the interior of the canister.

* * * * *